United States Patent
Patchornik et al.

(10) Patent No.: US 12,091,445 B2
(45) Date of Patent: *Sep. 17, 2024

(54) METHODS OF PURIFYING ANTIBODIES

(71) Applicants: Ariel Scientific Innovations Ltd., Ariel (IL); Yeda Research and Development Co. Ltd., Rehovot (IL)

(72) Inventors: Guy Patchornik, Kiryat-Ono (IL); Irishi N. N. Namboothiri, Mumbai (IN); Mordechai Sheves, Rehovot (IL); Assaf Howard, Petach-Tikva (IL); Margalit (Maggie) Cohen, Petach-Tikva (IL)

(73) Assignees: Ariel Scientific Innovations Ltd., Ariel (IL); Yeda Research and Development Co. Ltd., Rehovot (IL)

( * ) Notice: Subject to any disclaimer, the term of this patent is extended or adjusted under 35 U.S.C. 154(b) by 1121 days.

This patent is subject to a terminal disclaimer.

(21) Appl. No.: 16/611,859

(22) PCT Filed: May 9, 2018

(86) PCT No.: PCT/IL2018/050506
§ 371 (c)(1),
(2) Date: Nov. 8, 2019

(87) PCT Pub. No.: WO2018/207184
PCT Pub. Date: Nov. 15, 2018

(65) Prior Publication Data
US 2020/0102372 A1 Apr. 2, 2020

Related U.S. Application Data

(60) Provisional application No. 62/503,977, filed on May 10, 2017.

(51) Int. Cl.
| | | |
|---|---|---|
| *C07K 16/06* | (2006.01) | |
| *C07K 1/14* | (2006.01) | |
| *C07K 16/36* | (2006.01) | |
| *C11D 9/22* | (2006.01) | |

(52) U.S. Cl.
CPC ............ *C07K 16/065* (2013.01); *C07K 1/14* (2013.01); *C07K 16/36* (2013.01); *C11D 9/22* (2013.01)

(58) Field of Classification Search
None
See application file for complete search history.

(56) References Cited

U.S. PATENT DOCUMENTS

| 2012/0053328 A1 | 3/2012 | Yan et al. |
| 2015/0216216 A1 | 8/2015 | Marga |
| 2017/0121668 A1 | 5/2017 | Sheves et al. |

FOREIGN PATENT DOCUMENTS

| CN | 1563090 | 1/2005 |
| CN | 102301235 | 12/2011 |
| WO | WO 2018/207184 | 11/2018 |
| WO | WO 2018/207184 A3 | 11/2018 |
| WO | WO 2021/033176 | 2/2021 |

OTHER PUBLICATIONS

Liu et al. 'Nanoparticle iron chelators: A new therapeutic approach in Alzheimer disease and other neurologic disorders associated with trace metal imbalance.' Neuroscience Letters 406:189-193, 2006.*
Dhandapani et al. Purification of antibody fragments via interaction with detergent micellar aggregates. Sci Rep . Jun. 3, 2021;11(1): 11697. doi: 10.1038/s41598-021-90966-1.*
'Engineered-membranes and engineered-micelles as efficient tools for purification of halorhodopsin and bacteriorhodopsin.'Analyst, 140, 204-21, 2015.*
Notification of Office Action and Search Report Dated Sep. 13, 2022 From the State Intellectual Property Office of the People's Republic of China Re. Application No. 201880045994.5 and Its Translation of Office Action Into English. (17 Pages).
Office Action Dated Sep. 22, 2022 From the Israel Patent Office Re. Application No. 268878. (4 Pages).
International Preliminary Report on Patentability Dated Nov. 21, 2019 From the International Bureau of WIPO Re. Application No. PCT/IL2018/050506. (9 Pages).
International Search Report and the Written Opinion Dated Nov. 12, 2018 From the International Searching Authority Re. Application No. PCT/IL2018/050506. (16 Pages).
Follman et al. "Factorial Screening of Antibody Purification Processes Using Three Chromatography Steps Without Protein A", Journal of Chromatography A, 1024(1): 79-85, Jan. 23, 2004.
Frenzel et al. "Expression of Recombinant Antibodies", Frontiers in Immunology, 4(Art.217): 1-20, Jul. 29, 2013.
Ghosh et al. "Purification of Humanized Monoclonal Antibody by Hydrophobic Interaction Membrane Chromatography", Journal of Chromatography A, 1107(1-2): 104-109, Available Online Jan. 18, 2006.
Guse et al. "Purification and Analytical Characterization of An Anti-CD4 Monoclonal Antibody for Human Therapy", Journal of Chromatography A, 661(1): 13-23, Feb. 11, 1994.
Kumar et al. "Purification of Histidine-Tagged Single-Chain Fv Antibody Fragments by Metal Chelate Affinity Precipitation Using Thermoresponsive Copolymers", Biotechnology and Bioengineering, XP002783967, 84(4): 494-503, Published Online Sep. 11, 2003. Abstract, p. 495, col. 2, Para 2, p. 496, col. 1, Para 2, col. 2, Para 2, 3.
Manzke et al. "Single-Step Purification of Bispecific Monoclonal Antibodies for Immunotherapeutic Use by Hydrophobic Interaction Chromatography", Journal of Immunological Methods, 208(1): 65-73, Oct. 13, 1997.
McDonald et al. "Selective Antibody Precipitation Using Polyelectrolytes: A Novel Approach to the Purification of Monoclonal Antibodies", Biotechnology and Bioengineering, XP003026475, 102(4): 1141-1151, Published Online Sep. 19, 2008. p. 1144, col. 2, Para —p. 1146.

(Continued)

Primary Examiner — Nora M Rooney

(57) ABSTRACT

A method of isolating an antibody is disclosed. The method comprises contacting a hydrophobic chelator, a non-ionic detergent and metal ions so as to generate an aggregate comprising the hydrophobic chelator, the detergent and the metal ions; and contacting the aggregate with a medium comprising the antibody under conditions that allow partitioning of the antibody into the aggregate. Kits for isolating the antibody are also disclosed.

16 Claims, 18 Drawing Sheets
(14 of 18 Drawing Sheet(s) Filed in Color)

(56) References Cited

OTHER PUBLICATIONS

Patchornik et al. "Purification of a Membrane Protein With Conjugated Engineered Micelles", Bioconjugate Chemistry, 24(7): 1270-1275, Jun. 13, 2013.
Invitation to Pay Additional Fees, Communication Relating to the Results of the Partial International Search and the Provisional Opinion Dated Jul. 20, 2020 From the International Searching Authority Re. Application No. PCT/IL2020/050452. (17 Pages).
Dhandapani et al. "A General Platform for Antibody Purification Utilizing Engineered-Micelles", mABS, XP055711155, 11(3): 583-592, Published Online Feb. 6, 2019.
Dhandapani et al. "Role of Amphiphilic [Metal:Chelator] Complexes in A Non-Chromatographic Antibody Purification Platform", Journal of Chromatography B: Biomedical Sciences & Applications, XP085922155, 1133: 121830-1-121830-10, Available Online Oct. 21, 2019.
English Translation Dated May 20, 2022 of Notice of Reasons for Rejection Dated May 10, 2022 From the Japan Patent Office Re. Application No. 2019-561788. (4 Pages).
Notice of Reasons for Rejection Dated May 10, 2022 From the Japan Patent Office Re. Application No. 2019-561788. (5 Pages).
Official Action Dated Nov. 12, 2021 from the US Patent and Trademark Office Re. U.S. Appl. No. 16/497,833. (9 pages).
Restriction Official Action Dated Jun. 1, 2021 from the US Patent and Trademark Office Re. U.S. Appl. No. 16/497,833. (13 pages).
Search Report and Written Opinion Dated Jan. 11, 2022 From the Intellectual Property Office of Singapore, IPOS Re. Application No. 11201909184R. (7 Pages).
Search Report and Written Opinion Dated Jun. 16, 2020 From the Intellectual Property Office of Singapore, IPOS Re. Application No. 11201909184R. (13 Pages).
Written Opinion Dated Mar. 23, 2021 From the Intellectual Property Office of Singapore, IPOS Re. Application No. 11201909184R. (10 Pages).
Hoogenkamp "Building A Better Hybrid Burger. New Technologies Open New Possibilities for the Production of Burgers—Part 2", FleischWirtschaft International, Product Development, p. 80-88, Feb. 2013.
Kaspar et al. "Sensory Evaluation of Sausages With Various Proportions of Cyprinus Carpio Meat", Czech Journal of Food Sciences, 33(1): 45-51, Feb. 2015.
Krona et al. "Developing Cultured Meat Scaffolds of Extruded Vegetable-Based Proteins", Annual Transactions of the Nordic Rheology Society, 25: 311-313, Apr. 3-6, 2017.
International Search Report and the Written Opinion Dated Oct. 19, 2020 From the International Searching Authority Re. Application No. PCT/IL2020/05452. (22 Pages).
Communication Pursuant to Article 94(3) EPC Dated Sep. 6, 2021 From the European Patent Office Re. Application No. 18732163.3. (8 Pages).
Translation Dated Apr. 11, 2023 of Grounds of Reason of Rejection Dated Mar. 20, 2023 From the Korean Intellectual Property Office Re. Application No. 10- 2019-7036438. (7 Pages).
Grounds of Reason of Rejection Dated Mar. 20, 2023 From the Korean Intellectual Property Office Re. Application No. 10-2019-7036438 (6 Pages).
Missirlis et al. "Mechanisms of Peptide Amphiphile Internalization by SJSA-1 Cells in Vitro", Biochemistry, 48: 3304-3314, 2009.
International Search Report and the Written Opinion Dated Sep. 22, 2022 From the International Searching Authority Re. Application No. PCT/IL2022/050818. (19 Pages).
Dhandapani et al. "Conjugated Detergent Micelles as a Platform for IgM Purification", Biotechnology and Bioengineering, 119(7): 1997-2003, Mar. 24, 2022.
Dhandapani et al. "Detergent Micelle Conjugates Containing Amino Acid Monomers Allow Purification of Human IgG Near Neutral pH", Journal of Chromatography B, 1206: 1-5, Jun. 28, 2022.
Dhandapani et al. "Nonionic Detergent Micelle Aggregates: An Economical Alternative to Protein A Chromatography", New Biotechnology, 61: 90-98,Dec. 3, 2021.
Dhandapani et al. "Purification of Antibody Fragments via Interaction with Detergent Micellar Aggregates", Scientific Reports, 11: 1-11, Jun. 3, 2021.

\* cited by examiner

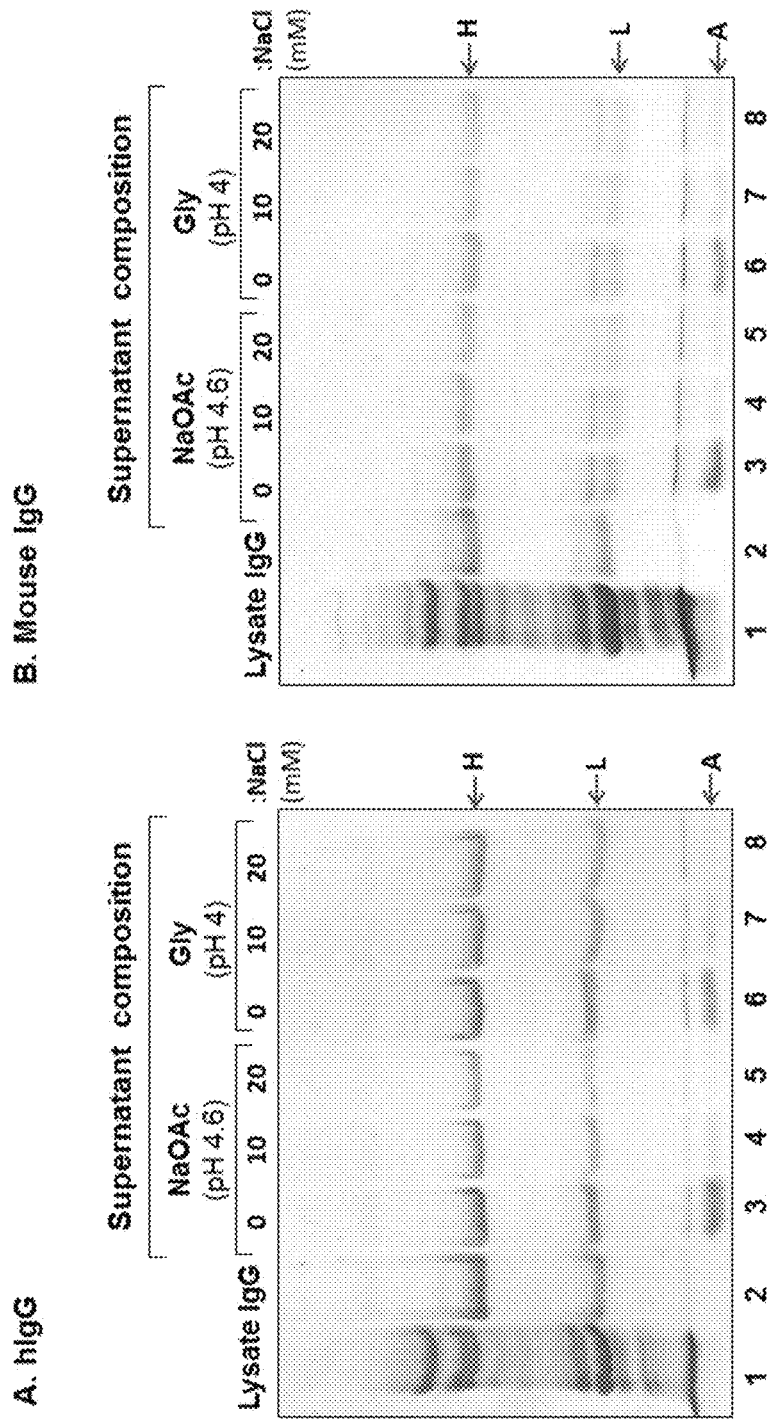

METHODS OF PURIFYING ANTIBODIES

RELATED APPLICATIONS

This application is a National Phase of PCT Patent Application No. PCT/IL2018/050506 having International filing date of May 9, 2018, which claims the benefit of priority under 35 USC § 119(e) of U.S. Provisional Patent Application No. 62/503,977 filed on May 10, 2017. The contents of the above applications are all incorporated by reference as if fully set forth herein in their entirety.

FIELD AND BACKGROUND OF THE INVENTION

The present invention, in some embodiments thereof, relates to methods and, kits for purifying antibodies.

Monoclonal antibodies (mAb's) are currently the recombinant proteins most commonly used as therapeutics; they were the largest selling class of biologics in the USA in 2012. The dramatic increase in their expression levels from low milligram to multi-gram concentration per liter, together with the multi-hundred kilogram to ton quantities in which some of them will be required, pose an on-going challenge for industrial purification methods capable of efficiently capturing mAb's from complex mixtures. This is generally achieved via ProA chromatography as the initial capturing step, commonly resulting in high recovery yields (~95%), purity (>95%), while removing the majority of host DNA, viral contaminants and leached ProA.

These remarkable features have made ProA chromatography the gold standard for antibody manufacturing. However, there is motivation for the development of more economic alternatives since ProA resins suffer from high costs relative to non-affinity polymeric supports (e.g. ion exchangers). This motivation is further justified when considering the current and future global biotech demands (i.e. many tons of purified mAb's per year) representing hundreds of different therapeutic mAb's under development, all aimed at targeting various cancers, autoimmune and inflammatory disorders.

It has been argued that, the use of ProA, and of chromatographic strategies in general, represent an inherent "productivity bottleneck" for industrial purification of mAb's, which can account for up to 80% of the total manufacturing cost thus making any antibody capturing method not entailing: (a) ProA as a ligand and/or (b) chromatography as the primary capturing step, an attractive alternative for future pharmaceutical needs.

Background art includes Patchornick et al., Bioconjugate Chemistry, 2013, Volume 24, pages 1270-1275; Guse et al., *J. Chromatogr A.* (1994) 661, 13-23; Manske et al., *J. Immunol Methods* (1997) 2008, 65-73; Follman and Fahrner *J. Chromatogr A.* (2004) 1024, 79-85 and Ghosh and Wang, *J. Chromatogr A.* (2006) 1107, 104-109.

SUMMARY OF THE INVENTION

A new concept for antibody purification was uncovered. Human immunoglobulin G (hIgG) and mouse IgG partition almost quantitatively (~95% by densitometry) into aggregates of non-ionic detergents, metal ions and hydrophobic chelators, whereas the majority (>85%, by densitometry) of non-IgG proteins (i.e. impurities), are rejected. The process was highly specific as it relies on the presence of the chelator and the metal. Antibodies that are adsorbed or embedded within the aggregates can be extracted without concomitant dissolution of the aggregates and lead to purer IgG preparations (~95% by densitometry). The overall yield of the process that includes: IgG partitioning and extraction range between ~40-46% (by densitometry). Circular dichroism spectroscopy (CD) demonstrated preservation of the secondary structure of extracted hIgG's.

According to an aspect of some embodiments of the present invention there is provided a method of isolating an antibody, the method comprising:
(a) contacting a hydrophobic chelator, a non-ionic detergent and metal ions so as to generate an aggregate comprising the hydrophobic chelator, said detergent and the metal ions; and
(b) contacting the aggregate with a medium comprising the antibody under conditions that allow partitioning of the antibody into the aggregate, thereby isolating the antibody.

According to an aspect of some embodiments of the present invention there is provided a kit comprising a hydrophobic chelator, a non-ionic detergent, a buffer having a pH between 3-6 and metal ions.

According to an aspect of some embodiments of the present invention there is provided a kit comprising a hydrophobic chelator, a polysorbate surfactant and metal ions.

According to some embodiments of the invention, the medium comprises a cell lysate.

According to some embodiments of the invention, the cell lysate is a whole cell lysate.

According to some embodiments of the invention, the cell lysate is devoid of organelles greater than about 2 microns.

According to some embodiments of the invention, the conditions of step (b) comprise having a level of salt below 100 mM.

According to some embodiments of the invention, the method further comprises solubilizing the antibody following step (b).

According to some embodiments of the invention, the solubilizing is effected with a buffer having a pH between 3-6.

According to some embodiments of the invention, the solubilizing is effected with a buffer having a pH between 3.8 and 4.

According to some embodiments of the invention, the buffer further comprises a salt.

According to some embodiments of the invention, the kit further comprises a buffer having a pH between 3-6.

According to some embodiments of the invention, the buffer is a carboxylic buffer.

According to some embodiments of the invention, the carboxylic buffer is selected from the group consisting of isoleucine, valine, glycine and sodium acetate.

According to some embodiments of the invention, the buffer comprises an amino acid.

According to some embodiments of the invention, the non-ionic detergent is a polysorbate surfactant.

According to some embodiments of the invention, the polysorbate surfactant is selected from the group consisting of polysorbate 20, polysorbate 40, polysorbate 60 and polysorbate 80.

According to some embodiments of the invention, the hydrophobic chelator comprises 8-Hydroxyquinoline.

According to some embodiments of the invention, the hydrophobic chelator comprises a phenanthroline.

According to some embodiments of the invention, the phenanthroline is selected from the group consisting of N-(1,10-Phenanthrolin-5-yl)methanamide) (Phen-C1), N-(1,10-Phenanthrolin-5-yl)ethanamide) (Phen-C2), N-(1, 10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), N-(1,10-Phenanthrolin-5-yl)nonanamide) (Phen-C9) and N-(1,10-Phenanthrolin-5-yl)decanamide) (Phen-C10).

According to some embodiments of the invention, the phenanthroline is selected from the group consisting of bathophenanthroline, N-(1,10-Phenanthrolin-5-yl)hexanamide) (Phen-6), N-(1,10-Phenanthrolin-5-yl)decanamide) (Phen-C10) and N-(1,10-Phenanthrolin-5-yl)octanamide) (Phen-C8).

According to some embodiments of the invention, the phenanthroline is bathophenanthroline.

According to some embodiments of the invention, the metal ion is a divalent metal ion.

According to some embodiments of the invention, the divalent metal ion is selected from the group consisting of $Zn^{2+}$, $Fe^{2+}$, $Mn^{2+}$, $Ni^{2+}$ and $Co^{2+}$.

According to some embodiments of the invention, the divalent metal ion is selected from the group consisting of $Zn^{2+}$ and $Fe^{2+}$.

According to some embodiments of the invention, the hydrophobic chelator is present in the aqueous solution at a concentration in the range of about 0.1% to about 10% (v/v).

According to some embodiments of the invention, the medium comprises a hybridoma medium.

According to some embodiments of the invention, the medium comprises serum albumin.

According to some embodiments of the invention, the metal ion is present in the aqueous at a concentration in the range of about 0.1% about 10% (v/v).

According to some embodiments of the invention, the cell lysate is derived from a bacterial cell.

According to some embodiments of the invention, the cell lysate is derived from a mammalian cell.

According to some embodiments of the invention, the mammalian cell is a Chinese Hamster Ovary cell (CHO).

According to some embodiments of the invention, the antibody is a humanized antibody.

According to some embodiments of the invention, the antibody is a recombinant antibody.

According to some embodiments of the invention, the antibody is selected from the group consisting of IgA, IgD, IgE, IgM and IgG.

According to some embodiments of the invention, the IgG is IgG1, IgG2, IgG3 or IgG4.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 6A-C illustrate SDS-PAGE and CD analysis. A. Extraction of hIgG from Tween-20 aggregates. Lane 1: *E. coli* lysate; lane 2: Target hIgG; lanes 3-8: supernatant composition after incubation with indicated buffer and salt concentrations B. as in A, but in the presence of mouse IgG. The gel is coomassie stained. C. CD analysis of hIgG extracted from Tween-20 aggregates in the presence of 50 mM AcOH (pH 4.6) in 20 mM NaCl.

DESCRIPTION OF SPECIFIC EMBODIMENTS OF THE INVENTION

The present invention, in some embodiments thereof, relates to methods and, kits for purifying antibodies. In particular, the methods relate to an alternative route for antibody capturing without the use of the common ligand, Protein A (ProA).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Purification of antibodies typically uses Protein A (proA) chromatography as the initial capturing step. However, proA chromatography is very expensive creating a "productivity bottleneck".

Figure 1:
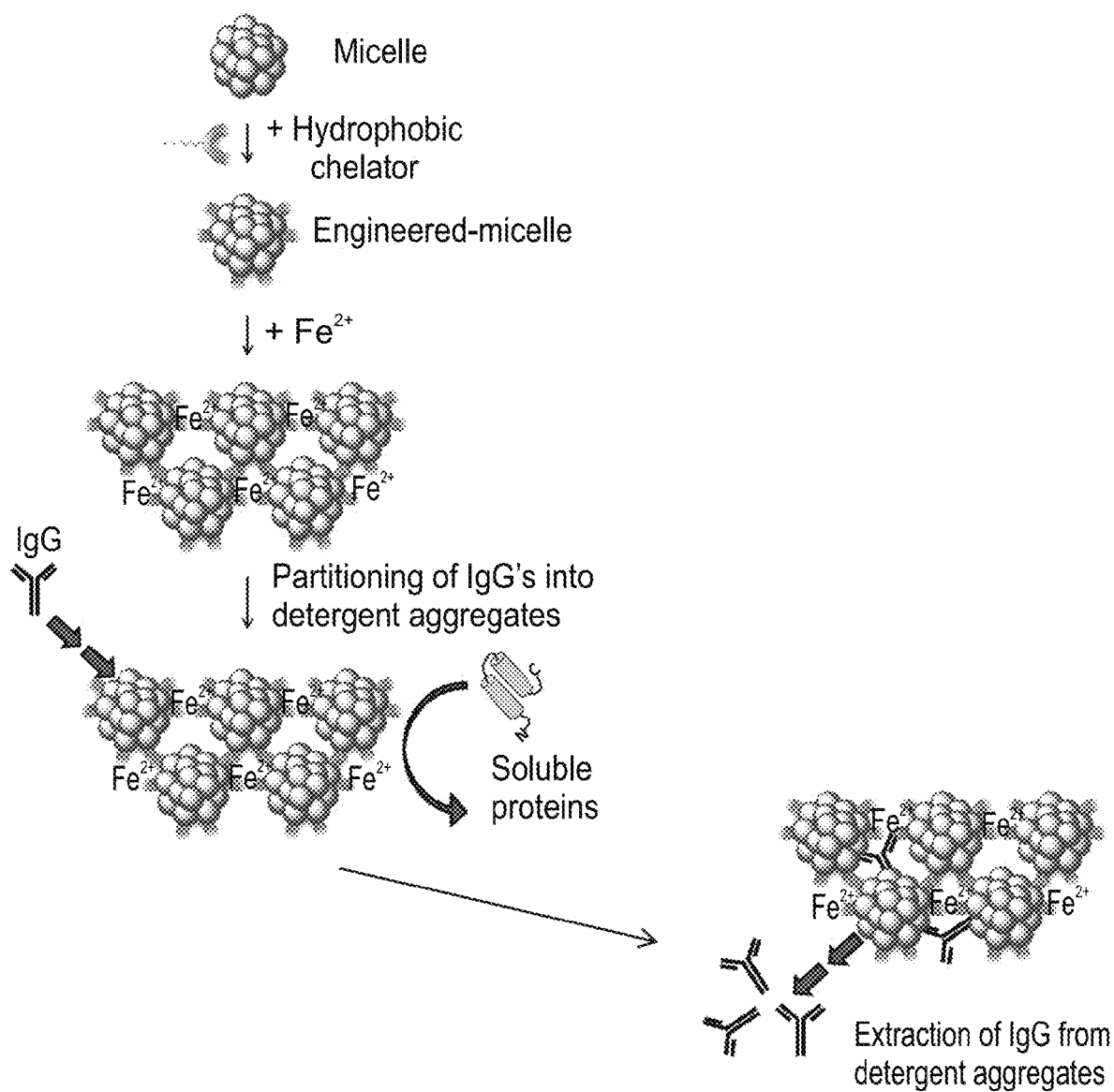
FIG. 1 is a schematic representation of the method disclosed herein according to embodiments of the present invention. Micelles composed of non-ionic detergents are transformed into engineered micelles upon incubation with a hydrophobic chelator and specifically cluster in the presence of $Fe^{2+}$ ions, thereby forming micellar aggregates interconnected by [metal:chelator] complexes. Antibodies partition into the micellar aggregate whereas other, more hydrophilic proteins, do not. Further extraction of the target IgG is accomplished under defined conditions that keep the detergent aggregate intact.
Figures 2A, 2B:
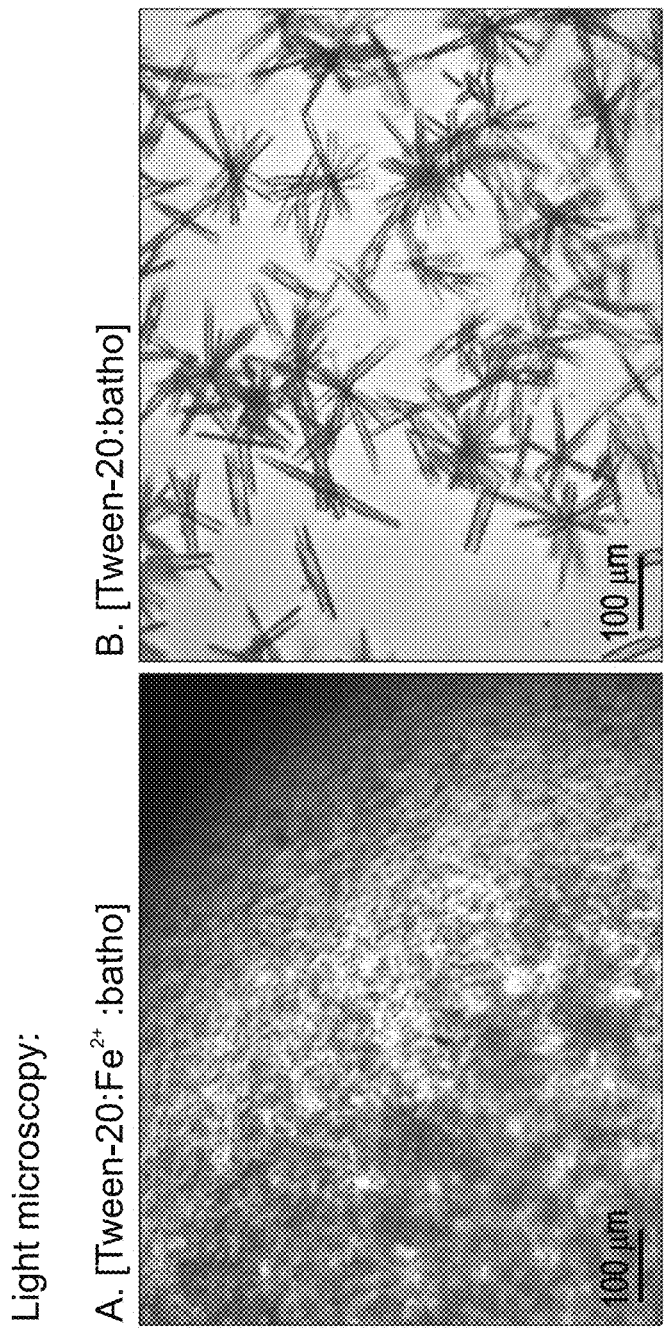
FIGS. 2A-D are photographs illustrating the effect of light microscopy and cryo-TEM analysis. Light microscopy: A. Tween-20 micelles conjugated via the [(bathophenanthroline)$_3$:$Fe^{2+}$] red complex. B. Control experiment, as in A but in the absence of $Fe^{2+}$. Cryo-TEM: C. Tween-20 micelles conjugated via the [(bathophenanthroline)$_3$:$Fe^{2+}$] complex. D. Control experiment containing only Tween-20 micelles (black dots).
Figures 2C, 2D:
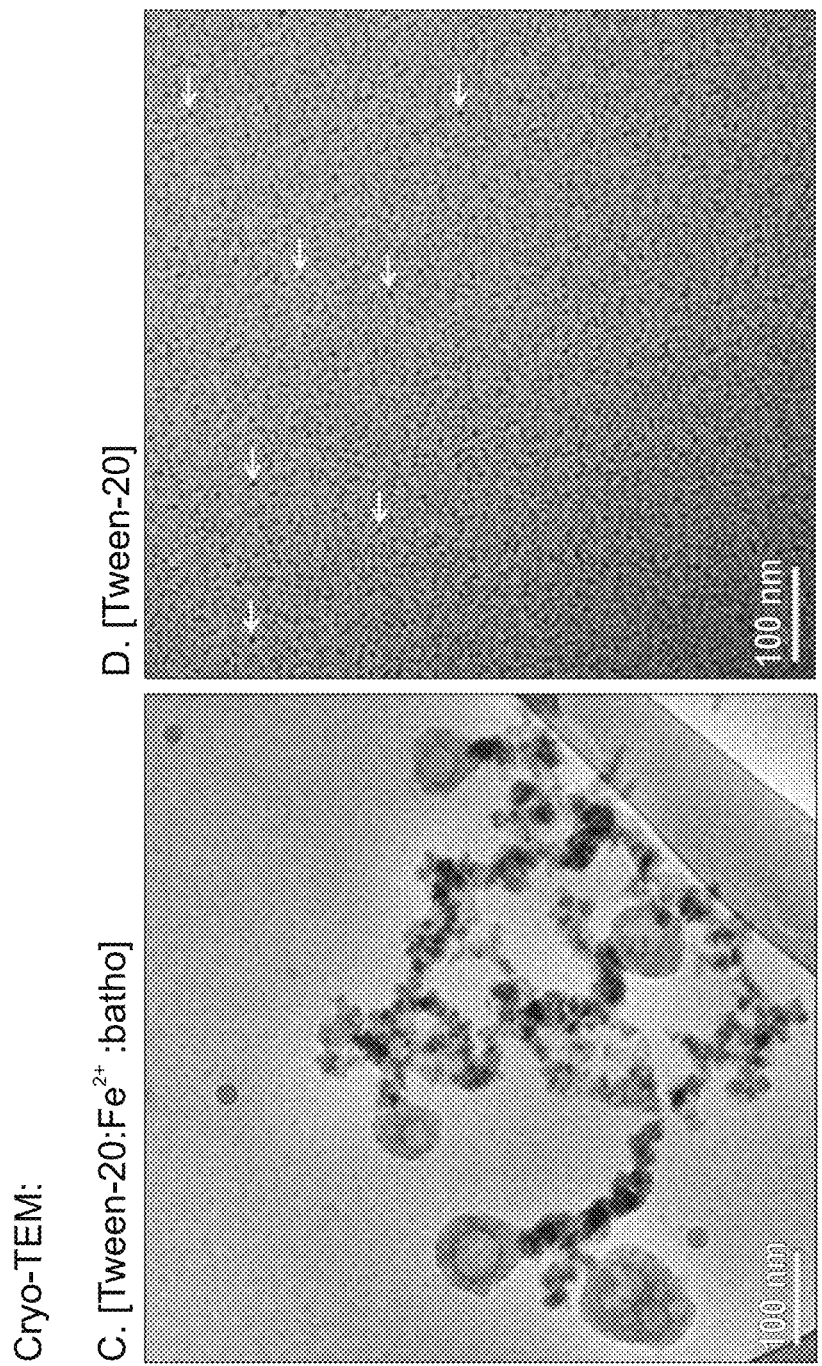

The present inventors therefore looked for alternatives for purifying IgG's. Although antibodies are highly hydrophilic, the present inventors surprisingly discovered that conjugated Tween-20 (Polysorbate 20) micelles, typically used to isolate hydrophobic proteins, could also be used as an alternative to the commonly used ProA columns for isolating antibodies. Their experimental findings demonstrate that micelles comprised of the non-ionic detergent Tween-20, can be specifically conjugated in the presence of the hydrophobic [(bathophenanthroline)$_3$:Fe$^{2+}$] red complex, leading to granular red precipitates (FIG. 2A). Micellar conjugation was found to be highly specific as it did not occur in the absence of either the metal (FIG. 2B) or the chelator (not shown). Analysis of the red-colored aggregates with cryo-TEM show that the [(bathophenanthroline)$_3$:Fe$^{2+}$] complex leads to various aggregational forms, some of which reach 100 nm (FIG. 2C) in size, whereas in the absence of the complex, the micellar dispersion appears monodisperse (FIG. 2D). These results provide direct evidence for the ability of the [(bathophenanthroline)$_3$:Fe$^{2+}$] complex to induce micellar clustering.

Figure 3A:
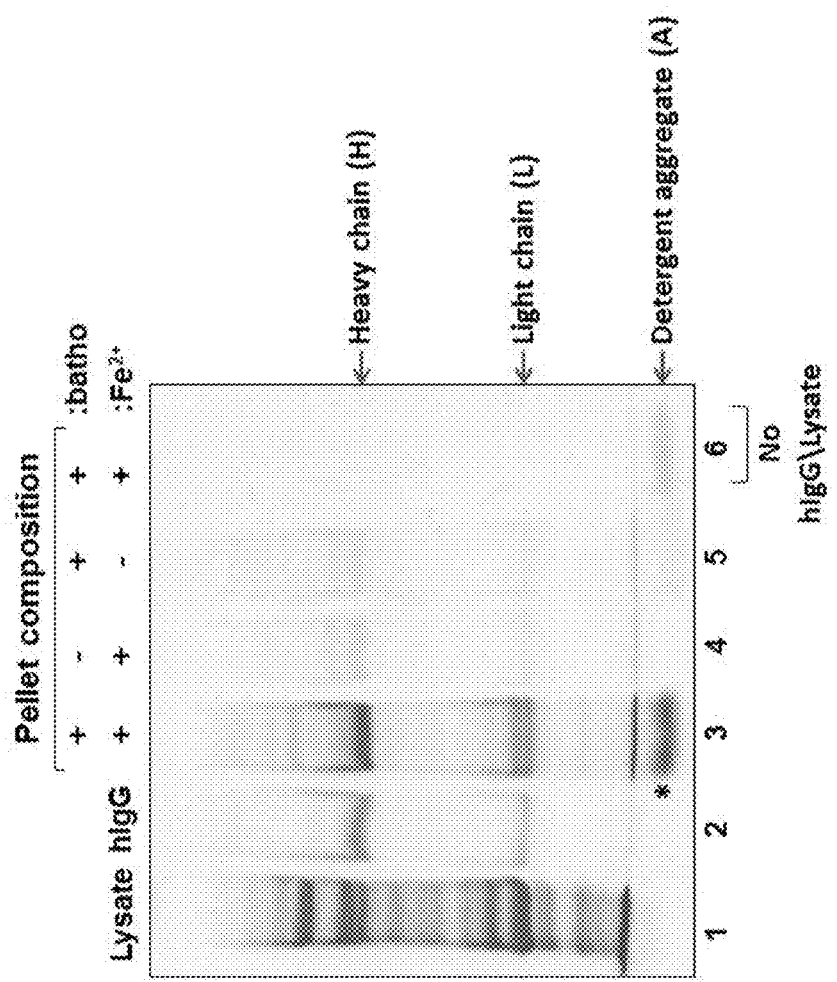
FIGS. 3A-C are photographs illustrating the results of SDS-PAGE analysis. A. Process viability and dependence on the metal and the chelator. Lane 1: *E. coli* lysate; lane 2: Target hIgG; lane 3: pellet composition in the presence of the [(bathophenanthroline)$_3$:$Fe^{2+}$] complex; lanes 4-5: as in lane 3 but in the absence of the chelator and metal, respectively; lane 6: Tween-20 aggregates in the absence of any added protein. The asterisk in lane 3 marks the stained Tween-20 aggregate devoid of any protein. The gel is Coomassie stained. B. Effect of ionic strength on purification of hIgG. Lanes 3-8 Purification of hIgG was conducted at indicated NaCl concentrations. C. Effect of ionic strength on purification of mouse IgG. Lanes 3-8 as in B.

To demonstrate IgG purification, a mixture of a target human IgG in *E. coli* lysate (which served as an artificial contamination background) was added to preformed Tween-20 aggregates. After a five minute incubation, the mixture was centrifuged and impurities present in the supernatant, were discarded. Analysis of the pellet by SDS-PAGE revealed the presence of the reduced heavy and light chains (FIG. 3A, lane 3). Moreover, the vast majority of impurities present in the system (FIG. 3A, lane 1) were absent in the pellet (FIG. 3A, lane 3), consistent with the hypothesis that water-soluble proteins other than IgG (which are on average more polar than IgG), would not associate with Tween-20 aggregates whereas antibody molecules would associate.

To demonstrate the generality of the process, the present inventors studied the dependence of IgG partitioning behavior with polyclonal mouse IgG as well (FIG. 3C) and found a very similar pattern. The fact that IgG from different biological origins (human and mouse) partition efficiently into Tween-20 aggregates implies that the present purification strategy may be independent of the particular amino acid sequence of the target IgG. This, in turn, may circumvent the need to develop specific purification protocols for each therapeutic monoclonal antibody and thus, a standardized purification platform may be achieved.

Figure 6C:
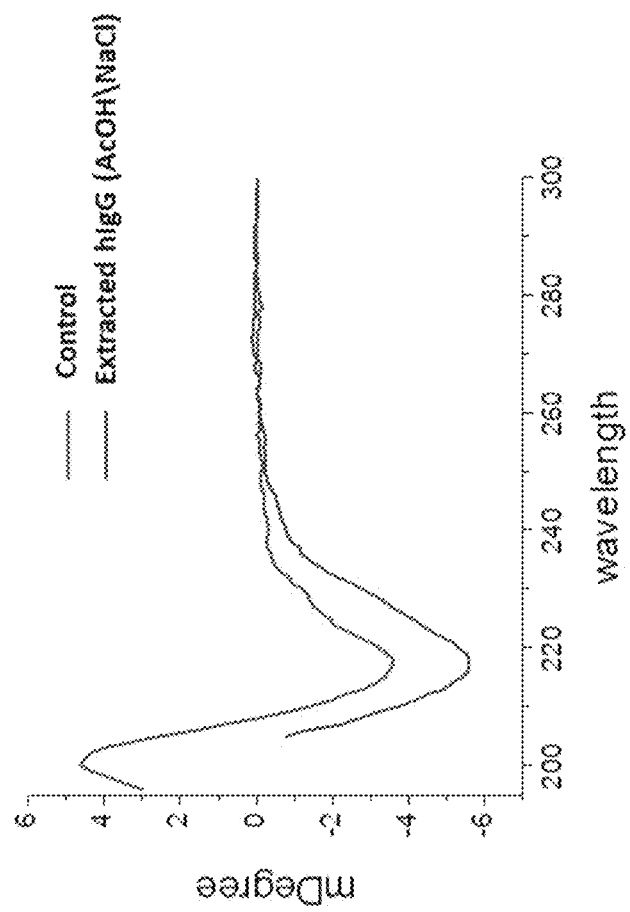

Two exemplary buffer systems (NaOAc pH 4.6 and Gly pH 4) demonstrated their capability in extracting hIgG and mouse IgG from Tween-20 aggregates while significantly suppressing aggregate dissolution and concomitant extraction of hydrophobic impurities (FIGS. 6A-B). Preservation of the secondary structure of hIgG was studied with circular dichroism (CD) (FIG. 6C). The CD analysis indicates that, no significant changes occurred in the secondary structure of purified hIgG (FIG. 6C).

Figure 8A:
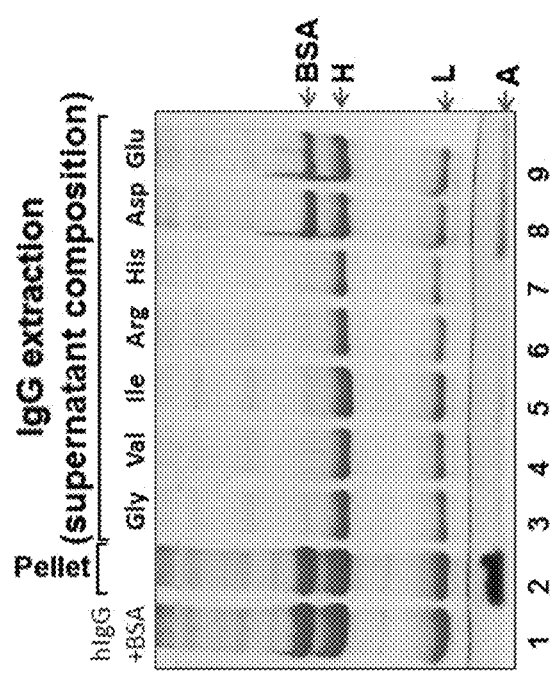
FIGS. 8A-E illustrate extraction buffer efficiency, circular dichroism analysis and DLS analysis. A. Effect of buffer composition on hIgG extraction. Lane 1: hIgG and BSA; lane 2: Pellet composition obtained after incubating Tween-20 aggregates with hIgG (1 mg\ml) and BSA (0.5 mg\ml) in serum free-media as described in the Experimental; lanes 3-9: Supernatant composition after extracting hIgG from pellets generated under conditions shown in lane 2 with buffers containing indicated amino acids at pH 3.8 as described in the Experimental. The letters: H & L represent the reduced Heavy and Light chains of the target antibody, respectively. The letter A, points at the detergent aggregate band. Gels are coomassie stained. B-C. Dynamic light scattering (DLS) analysis of human and mouse IgG's that were subjected to purification with Tween-20 aggregates and extracted with indicated buffers at pH 3.8 (dotted lines) vs. identical IgG's, not subjected to any purification serving as the control (black line). D. Circular dichroism (CD) absorption of: control (untreated) hIgG—straight line vs. purified hIgG—dotted line. E. As in D, but with mouse IgG.
Figure 8B:
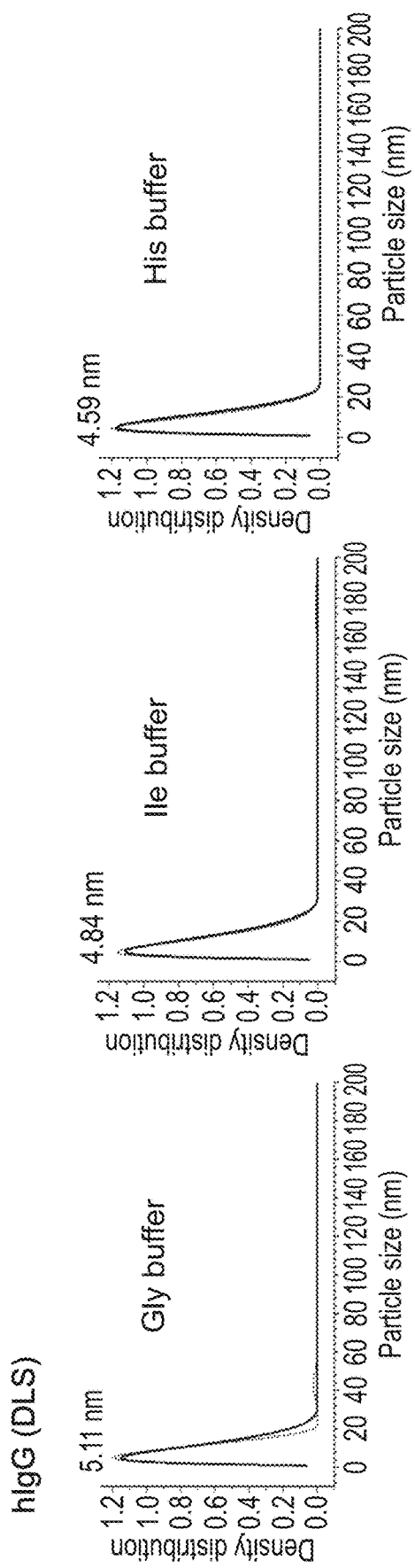
Figure 8C:
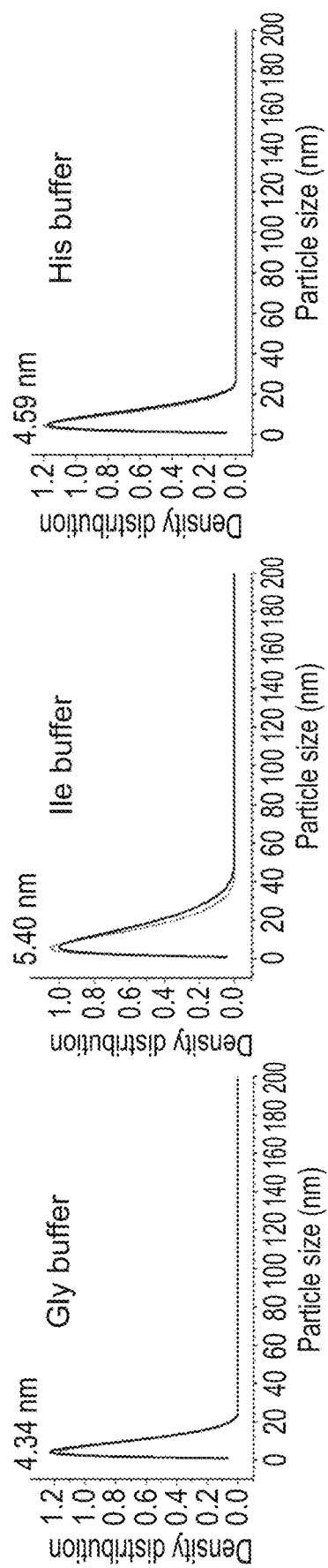
Figure 8E:
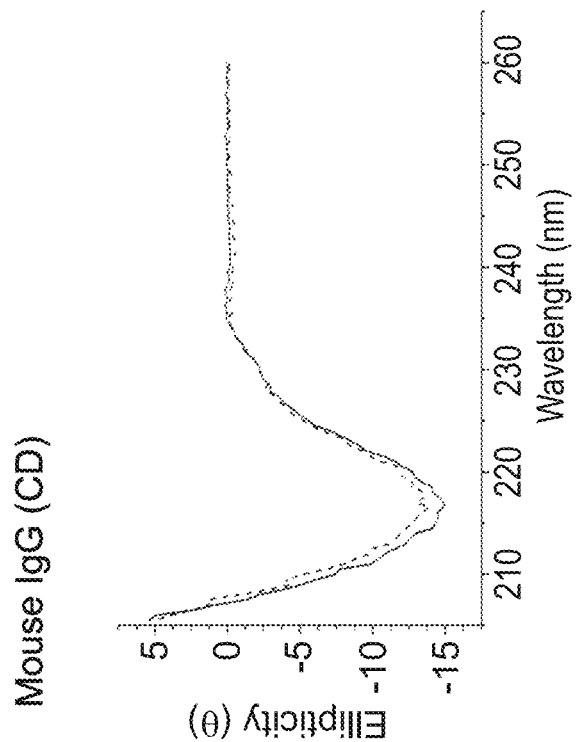

Other buffer systems were also shown to be able to extract hIgG and mouse IgG from Tween-20 aggregates—see FIG. 8A.

Whilst further reducing the present invention to practice, the present inventors showed that the purification strategy could also be used to purify antibodies from hybridoma serum-free media (FIGS. 7A-D).

Figures 9A, 9B:
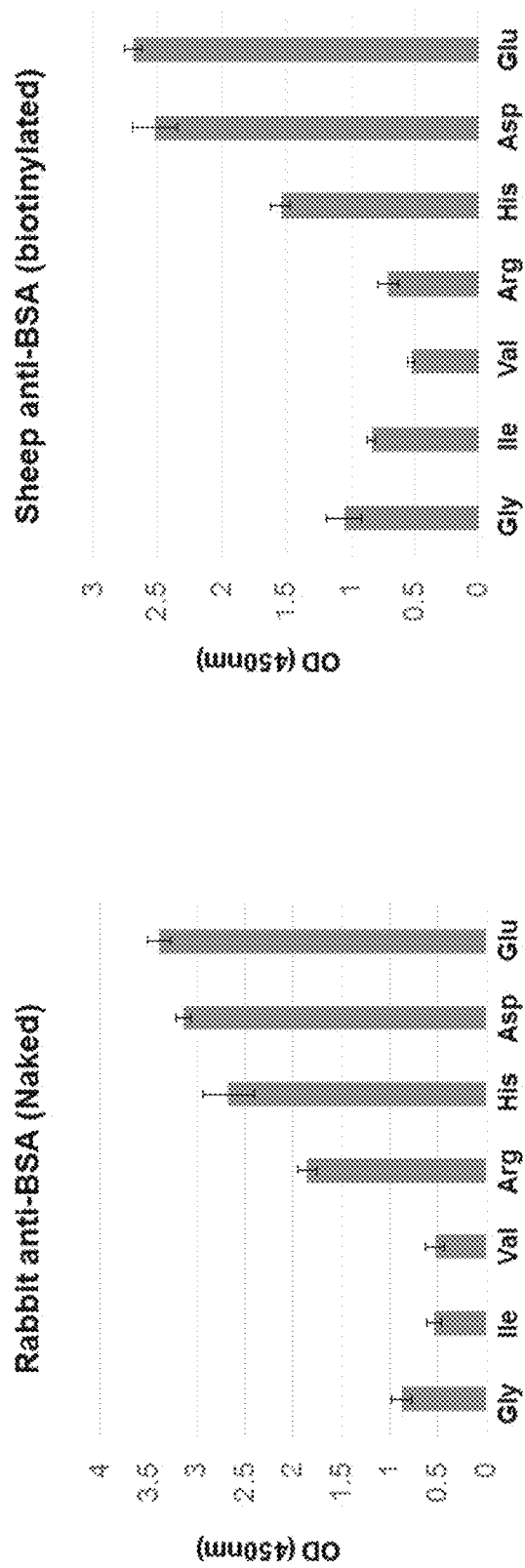
FIGS. 9A-B: ELISA analysis of extracted IgG's. Polyclonal anti-BSA IgG's originating from rabbit (naked) or sheep (biotinylated) were subjected to the presented purification method and extracted at 32° C. (5 min.) from Tween-20 aggregates with indicated amino acid buffers (50 mM) at pH 3.8. The ability of these purified Ab's to bind their target epitopes on BSA was determined by ELISA assays as described in the Materials and methods. The data presented relies on at least 12 independent experiments.

The present inventors antibodies remained active following purification (see FIGS. 9A-B).

Figures 10A, 10B:
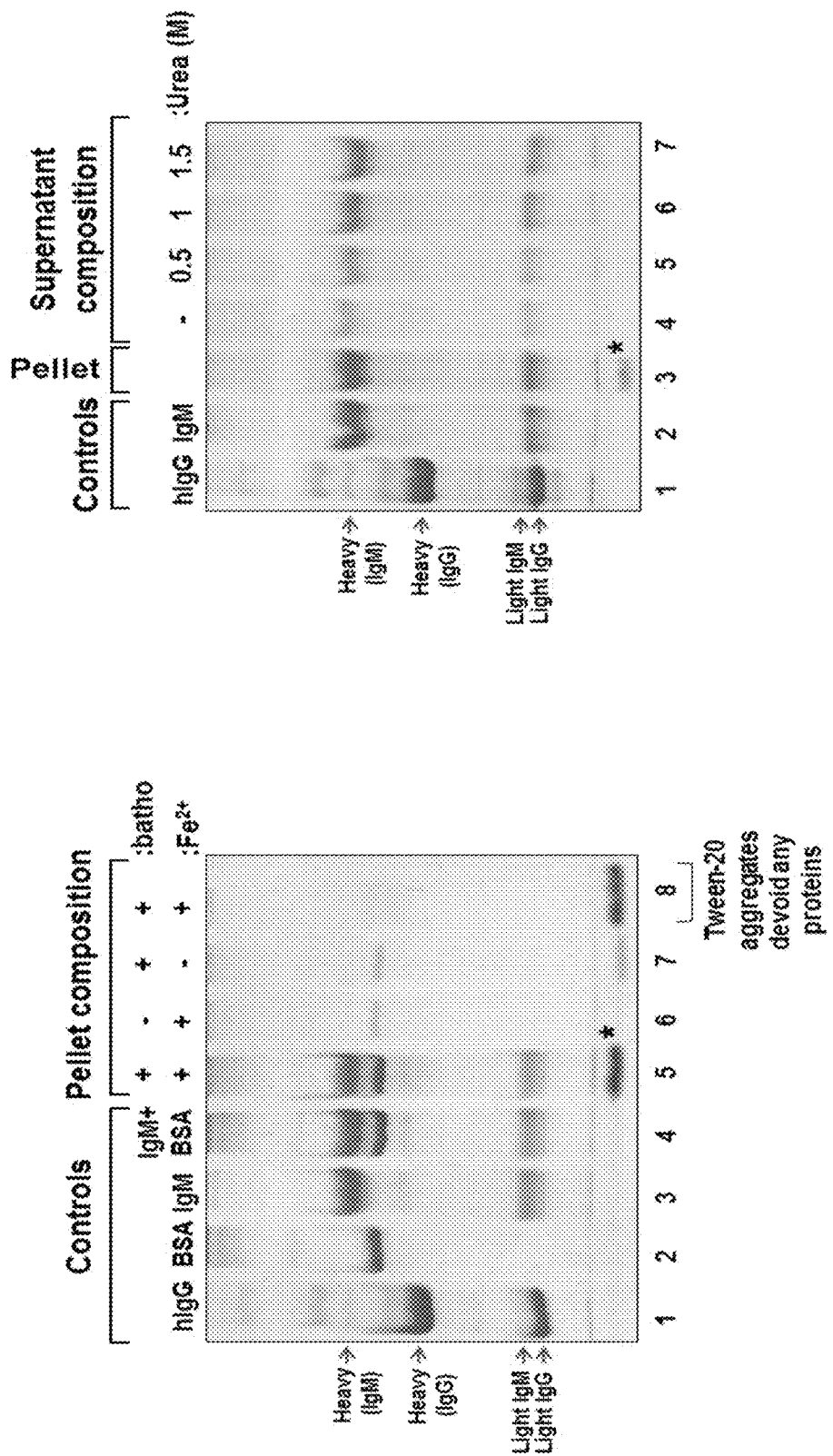
FIGS. 10A-B. Purification of IgM with Tween-20 aggregates. A. Specificity of IgM capture. Lane 1: hIgG; lane 2: BSA; lane 3: Bovine polyclonal IgM; lane 4: IgM+BSA mixture (total amount used); lane 5: Pellet composition after incubating the IgM+BSA mixture with [Tween-20:batho:Fe2+] aggregates and removal of the supernatant. The asterisk points at stained Tween-20 aggregates; lanes 6-7: As in lane 5, but in the absence of only the chelator (batho) or only the metal (Fe2+), respectively; lane 8: Pellet comprised of: [Tween-20:batho:Fe2+] aggregates devoid of any added protein. B. IgM extraction. Lane 1: hIgG; lane 2: Bovine polyclonal IgM; lane 3: Pellet composition after incubating IgM with [Tween-20:batho:Fe2+] aggregates and removal of the supernatant. The asterisk points at stained Tween-20 aggregates; lanes 4-7: Supernatant composition after incubating Tween-20 pellets containing IgM with indicated urea concentration at pH 3. Both gels are coomassie stained.

In addition, the present inventors showed that the purification protocol was not only effective for monomeric antibodies (IgG) but also for pentameric antibodies (IgM)—see FIGS. 10A-B.

The purification strategy presented here possesses several inherent advantages: (A) reduction in raw material costs; (B) lower purification yields due to ligand denaturation is irrelevant since no specific ligand is involved; (C) the limited capacity of affinity columns (currently 30 gr\L) is not applicable to the current technology, since it does not rely on the use of columns and affinity resins; and (D) speed—the large-scale antibody purification process currently used requires 1-2 days. It is likely that removal of one (or two) chromatographic steps would significantly shorten the overall purification time and with it, the production efficiency.

Thus, according to a first aspect of the present invention there is provided a method of isolating an antibody, the method comprising:
(a) contacting a hydrophobic chelator, a non-ionic detergent and metal ions so as to generate an aggregate comprising the hydrophobic chelator, the detergent and the metal ions; and
(b) contacting the aggregate with a medium comprising the antibody under conditions that allow partitioning of the antibody into the aggregate, thereby isolating the antibody.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen.

Suitable antibody fragments contemplated by the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883. 1989.), a compromise between Kabat and Chothia using Oxford Molecular's AbM antibody modeling software (now Accelrys™, see, Martin et al., 1989, Proc. Natl Acad Sci USA. 86:92689 and world wide web site www(dot)bioinf-org(dot)uk/abs), available complex crystal structures as defined by the contact definition (see MacCallum et al., J. Mol. Biol. 262:732-745, 1996) and the "conformational definition" (see. e.g., Makabe et al., Journal of Biological Chemistry, 283:1156-1166, 2008).

As used herein. the "variable regions" "CDRs" may refer to variable regions and CDRs defined by any approach known in the art, including combinations of approaches.

Functional antibody fragments comprising whole or essentially whole variable regions of both light and heavy chains are defined as follows:
(i) Fv, defined as a genetically engineered fragment consisting of the variable region of the light chain (VL) and the variable region of the heavy chain (VH) expressed as two chains;
(ii) single chain Fv ("scFv"), a genetically engineered single chain molecule including the variable region of the light chain and the variable region of the heavy chain, linked by a suitable polypeptide linker as a genetically fused single chain molecule.
(iii) disulfide-stabilized Fv ("dsFv"), a genetically engineered antibody including the variable region of the light chain and the variable region of the heavy chain, linked by a genetically engineered disulfide bond.
(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;
(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);
(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and
(vii) Single domain antibodies or nanobodies are composed of a single VH or VL domains which exhibit sufficient affinity to the antigen.

In one embodiment, the antibody is a polyclonal antibody.

In another embodiment, the antibody is a monoclonal antibody.

In still a further embodiment, the antibody is a recombinant antibody.

In still a further embodiment, the antibody is a humanized antibody.

In still further embodiments, the antibody is IgA, IgD, IgE and IgG (e.g. IgG1, IgG2, IgG3 or IgG4).

In still further embodiments, the antibody is IgM.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly.

These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin.

Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)].

Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

When using recombinant techniques, the antibody can be produced intracellularly, in the periplasmic space, or directly secreted into the medium. If the antibody is produced intracellularly, as a first step, the particulate debris, either host cells or lysed cells, can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Lysis of the cells may be performed by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration.

As used herein, the term "cell lysate" refers to an aqueous solution of cellular biological material which comprises the antibody, wherein a substantial portion of the cells of the cellular material have become disrupted and released their internal components.

In one embodiment, the cell lysate is prepared from whole cells.

In the case of a whole cell lysate, it will be appreciated that following cell membrane disruption, the cell lysate may be treated so as to remove organelles greater than about 2 microns (e.g. cell nucleii). Thus, for example the whole cell lysate may be centrifuged so as to precipitate cell nucleii from the cell lysate. Exemplary centrifugation conditions include 1-5 minutes at 500-1000×g (e.g. 2 min. at 985×g).

The cell lysate may be prepared from any cell that expresses an antibody. The cells may be eukaryotic (e.g. mammalian, plant, fungus) or prokaryotic (bacteria).

In one embodiment, the cells secrete antibody into the cytoplasm thereof.

The cell may be genetically modified so as to express the antibody. In another embodiment, the cell is not genetically modified.

Exemplary cells that are contemplated include, but are not limited to gram negative bacterial cells, such as *E. Coli;* gram positive bacterial cells such as *Bacillus brevis, Bacillus subtilis, Bacillus megaterium* and Lactobacilli (e.g. *Lactobacillus zeae/casei* or *Lactobacillus paracasei*); yeast cells such as *Pichia pastoris, Saccharomyces cerevisiae, Hansenula polymorpha, Schizosaccharomyces pombe, Schwanniomyces occidentalis, Kluyveromyces lactis,* and *Yarrowia lipolytica;* filamentous fungii such as *Trichoderma* and *Aspergillus;* insect cells; mammalian cells including Chinese hamster ovary (CHO) cells and plant cells.

In one embodiment, the cells have been immortalized and are part of a cell line—e.g. hybridoma. As mentioned, the isolation method of this aspect of the present invention is carried out by contacting the medium comprising the antibody with aggregates of non-ionic detergent, hydrophobic chelator and metal ions.

Examples of cell media for culturing antibody producing cells include hybridoma media—e.g. serum-free hybridoma media. Such media are readily available from Companies such as Gibco, Thermo Fisher Scientific and Sigma-Aldrich.

In one embodiment, the media comprises a serum albumin such as horse serum albumin (HAS) or bovine serum albumin (BSA).

Preferably the serum albumin is present at a concentration of less than 0.5 mg/ml—for example between 0.1-0.5 mg/ml.

Prior to this step, the medium may optionally be clarified.

As used herein, the term "clarified" refers to a sample (i.e. a cell suspension) having undergone a solid-liquid separation step involving one or more of centrifugation, microfiltration and depth filtration to remove host cells and/or cellular debris. A clarified fermentation broth may be a cell culture supernatant. Clarification is sometimes referred to as a primary or initial recovery step and typically occurs prior to any chromatography or a similar step.

The term "non-ionic detergent" refers to detergents that comprise uncharged, hydrophilic headgroups. Some non-ionic detergents are based on polyoxyethylene or a glycoside. Common examples of the former include Tween, Triton, and the Brij series. These materials are also known as ethoxylates or PEGlyates and their metabolites, nonylphenol. Glycosides have a sugar as their uncharged hydrophilic headgroup. Examples include octyl thioglucoside and maltosides. HEGA and MEGA series detergents are similar, possessing a sugar alcohol as headgroup.

According to a particular embodiment, the non-ionic detergent is a polysorbate surfactant. Examples of such include, but are not limited to of polysorbate 20, polysorbate 40, polysorbate 60 and polysorbate 80.

In one embodiment, the non-ionic detergent is polysorbate 20.

Other exemplary non-ionic detergents contemplated by the present invention include those that belong to the pluronic family e. g. F-68 and F-127.

As used herein, the term "chelator" refers to a compound which binds metal ions from solution, by the formation or presence of two or more separate co-ordinate bonds between a polydentate ligand and a single central atom. The chelator of this aspect of the present invention is capable of chelating the metal ion which is used for the isolation. Preferably, the chelator binds electrostatically (non-covalently) to the metal ion. According to a particular embodiment, the chelator is capable of chelating metal ions with a ratio of chelator to metal of 2:1 or greater.

The hydrophobicity of the chelator is such that it is capable of partitioning into the aggregates of the non-ionic detergent. In one embodiment, the chelator is capable of embedding into the aggregates of the non-ionic detergent.

In one embodiment, the hydrophobic chelator comprises at least 8 carbons (for example in a chain, or in a ring) and does not comprise charged groups.

In some embodiments, the hydrophobic chelator is 8-Hydroxyquinoline or a derivative thereof. Exemplary derivatives of 8-Hydroxyquinoline include, but are not limited to 2-methyl-8-hydroxyquinoline (CH3 -HQ), 5 ,7-dichloro-2-methyl- 8-hydroxyquinoline (C12-CH3 -HQ), 5,7-dibromo-8-hydroxyquinoline (Br2-HQ), 5-sulfo-7-iodo-8-hydroxyquinoline (ferron) and 5-sulfo-8-hydroxyquinoline (SO3H-HQ).

In some embodiments, the hydrophobic chelator comprises a phenanthroline, for example a 1,10-Phenanthroline. Other phenanothrolines are also contemplated which have not been substituted with hydrophilic substituents.

Exemplary hydrophobic phenanthrolines include, but are not limited to bathophenanthroline, and N-(1,10-Phenanthrolin-5-yl)alkylamide), with the alkyl being from 1-10 carbon atoms in length. Exemplary N-(1,10-Phenanthrolin-5-yl)alkylamide) compounds include N-(1, 10-Phenanthrolin-5-yl)methanamide) (Phen-C1), N-(1,10-Phenanthrolin-5-yl)ethanamide) (Phen-C2), N-(1,10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), N-(1,10-Phenanthrolin-5-yl)nonanamide) (Phen-C9), N-(1,10-Phenanthrolin-5-yl)decanamide) (Phen-C10).

In some such embodiments, the phenanthroline is selected from the group consisting of bathophenanthroline, N-(1,10-Phenanthrolin-5-yl)hexanamide) (Phen-6), N-(1,10-Phenanthrolin-5-yl)decanamide) (Phen-C10) and N-(1,10-Phenanthrolin-5-yl)octanamide) (Phen-C8).

Herein throughout, an "alkylamide" describes a —NH—C(=O)—R, wherein R is alkyl.

The term "alkyl" describes a saturated aliphatic hydrocarbon including straight chain and branched chain groups. Preferably, the alkyl group has 1 to 20 carbon atoms in length. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. The alkyl group may be substituted or unsubstituted. Substituted alkyl may have one or more substituents, whereby each substituent group can independently be, for example, alkyl, cycloalkyl, alkenyl, alkynyl, aryl, and heteroaryl. Additional substitutents may include, for example, hydroxyalkyl, trihaloalkyl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine, as long as the functionalities of the chelator are maintained.

In some embodiments, the phenanthroline is Phen-C10 or Phen-C8.

Additional examples of hydrophobic chelators include acidic organophosphorus chelators, for example DEHPA, EHEHPA and DTMPPA; neutral organophosphorus chelators, for example TBP and tri-n-octylphosphine oxide (TOPO), bifunctional organophosphorus chelators, for example CMPO and N,N,N',N'-tetraoctyl-3-oxamentanediamide (TOGDA); basic chelators, for example tri-n-octylamine (TOA) and tricaprylmethylammonium chloride. Other chelators known to those of skill in the art may also be used, including hydroxyoximes, for example 5,8-diethyl-7-hydroxy-6-dodecane oxime and 2-hydroxy-5-nonylacetophenon oxime, crown ethers, for example di-t-butyl-dicyclohexano-18-crown-6, and dithiosemicarbazone.

According to some embodiments, the hydrophobic chelator is present in the aqueous solution at a concentration in the range of about 0.1% to about 10% (v/v), such as, for example, about 0.5% to about 10% (v/v), about 1% to about 10% (v/v) such as for example about 5%, about 6%, about 7%, about 8%, about 9%, or about 10% of 20mM solution of chelator.

In some embodiments, the metal ion is a divalent metal ion.

In some embodiments, the divalent metal ion is selected from the group consisting of $Zn^{2+}$, $Fe^{2+}$, $Mn^{2+}$, $Ni^{2+}$ and $Co^{2+}$. Preferably, the divalent metal ion $Zn^{2+}$ or $Fe^{2+}$.

In some embodiments, the metal ion is present in the aqueous solution at a concentration in the range of about 0.1% to about 10% (v/v), such as, for example, about 0.5% to about 10% (v/v), about 1% to about 10% (v/v), about 5%, about 6%, about 7%, about 8%, about 9%, or about 10% of 50mM solution of metal ion.

The conditions of the incubation are such that aggregates are formed comprising the metal ion, the hydrophobic chelator and the non-ionic detergent.

Thus, for example, generation of aggregates is typically carried out at a temperature of about 0° C. to about 25° C. and more preferably from about 4° C. to about 25° C. The aggregates of this aspect of the present invention are typically between 10-500 nM, 10-200 nM, 1-100 mM or 10-100 mM.

The concentration of salt (e.g. NaCl) in the aggregates is typically, below 100 mM and more preferably below 50 mM. In one embodiment, the concentration of salt is below 40 mM, below 30 mM, below 20 mM, below 10 mM or even below 5 mM. Exemplary ranges include 20-100 mM, 20-50mM, 0-50mM, 0-40 mM, 0-30 mM, 0-25 mM, 0-20 mM. In one particular embodiment, the concentration of salt is about 25 mM.

In some embodiments, contacting the non-ionic detergent with a hydrophobic chelator is performed prior to contacting with a metal ion.

In other embodiments, contacting the non-ionic detergent with a hydrophobic chelator is performed concomitantly to contacting with a metal ion.

In still further embodiments, the hydrophobic chelator is contacted initially with the metal ion and then subsequently with the non-ionic detergent. Once aggregates are formed, they are contacted with the cell lysate under conditions that allow partitioning of the antibody (present in the cell lysate) into the aggregate.

Once this happens (seconds to hours—for example 5 minutes to 1 hour), precipitation of the complex may be facilitated by centrifugation (e.g. ultra-centrifugation), although in some cases (for example, in the case of large complexes) centrifugation is not necessary or very mild centrifugation can be used (so at to render the solution more dense—e.g. for 1-5 minutes at a speed of 13K).

Following precipitation, the antibody may be released from the pelleted complex i.e. solubilized.

Initially, the pellet may be washed—for example in a low salt solution (e.g. below 50 mM e.g. 20 mM NaCl solution).

Extraction may be effected with a buffer having a pH between 3-6, and more preferably between 3.8-5. In one embodiment, the buffer is a carboxylic buffer, examples of which include, but are not limited to sodium acetate and sodium citrate. An exemplary pH of sodium acetate is about pH 4.6.

In another embodiment, the buffer comprises an amino acid. In one embodiment, the buffer comprises a single amino acid. In another embodiment, the buffer comprises at least two amino acids.

In one embodiment, the amino acid is one which can competes for (i) hydrophobic interactions between the antibody side chains and the detergent aggregate (e.g. valine or isoleucine); (ii) ionic and/or H-bond interactions between the antibody side chains and the detergent aggregate (e.g. aspartic acid, glutamic acid or arginine); or (iii) metal chelation interactions between the antibody side chains and the detergent aggregate (e.g. histidine).

In a particular embodiment, the amino acid buffer is glycine, valine or isoleucine. In another embodiment, the amino acid buffer is isoleucine.

An exemplary pH of amino acid buffers is about pH 3.8 or pH 4.

The sample may be heated for a length of time that enhances extraction - for example (1-60 minutes), 1 minute, 5 minutes, 10 minutes. The temperature is selected such that it does not have an impact on the activity of the extracted antibody and does not cause the detergent aggregate to undergo dissolution. An exemplary temperature is between 25-35° C. According to a particular embodiment, the sample is heated for 5 minutes at 32° C.

To enhance the purity of the released antibody, salt may be added to the buffer (e.g. between 5-50 mM NaCl or 10-20 mM NaCl). To enhance the amount of antibody released from the complexed pellet, the present inventors contemplate using buffers which do not contain salt. It will be appreciated however, that the purity of the released antibody may then be compromised.

Depending on the intended use of the antibody that is isolated and optionally solubilized, the protein (either membrane or cytosolic) or agent that is bound thereto, may be subjected to further purification steps. This may be effected by using a number of biochemical methods which are well known in the art. Examples include, but are not limited to, fractionation on a hydrophobic interaction chromatography (e.g. on phenyl sepharose), ethanol precipitation, isoelectric focusing, reverse phase HPLC, chromatography on silica, chromatography on heparin sepharose, anion exchange chromatography, cation exchange chromatography, chromatofocusing, SDS-PAGE, ammonium sulfate precipitation, hydroxylapatite chromatography, gel electrophoresis, dialysis, viral inactivation (e.g. viral filtration) and ultrafiltration.

Figures 5A, 5B:
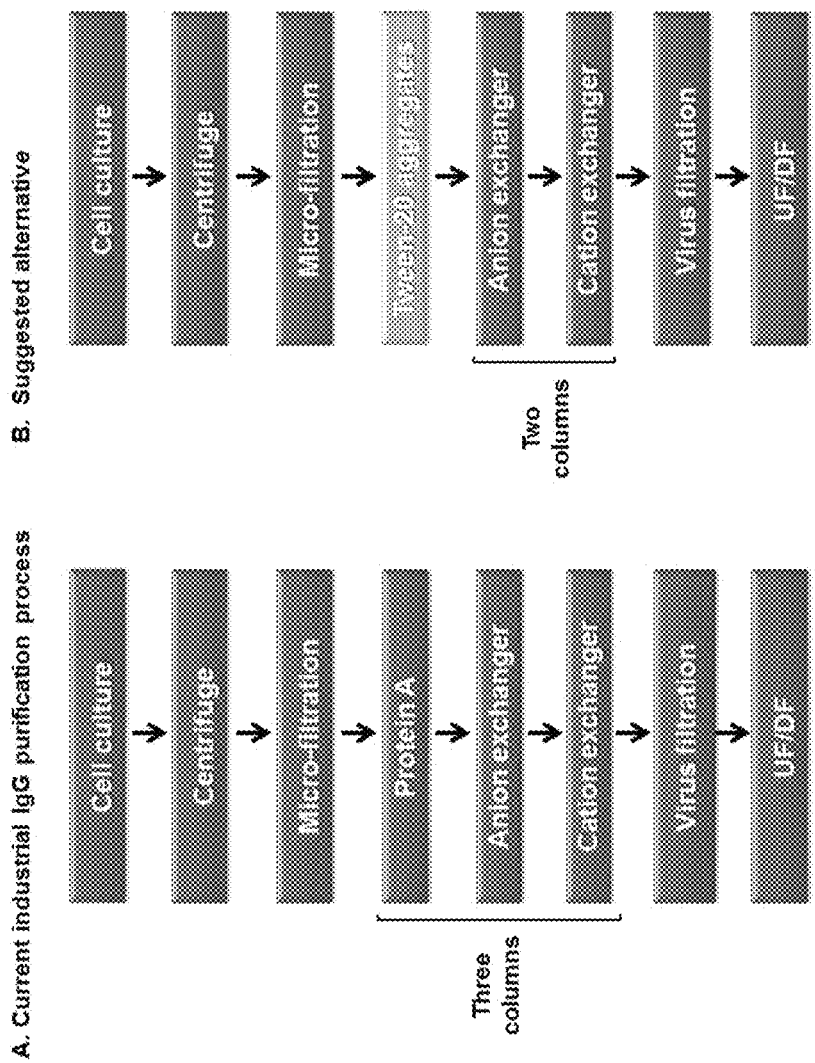
FIGS. 5A-B are schematic representations of the commonly used large-scale mAb purification process (A) and an alternative route utilizing Tween-20 aggregates (B). UF and DF represent ultrafiltration and diafiltration, respectively.

Examples of additional purification steps (and the order they may be carried out) are summarized in FIG. 5B.

Anion-exchange chromatography is a process that separates substances based on their charges using an ion-exchange resin containing positively charged groups, such as diethyl-aminoethyl groups (DEAE). In solution, the resin is coated with positively charged counter-ions (cations). Anion exchange resins will bind to negatively charged molecules, displacing the counter-ion.

Cation-exchange chromatography is a process that separates substances based on their charges using an ion-exchange resin containing negatively charged groups, such as carboxymethyl (CM), sulfoethyl(SE), sulfopropyl(SP), phosphate(P) and sulfonate(S). In solution, the resin is coated with negatively charged counter-ions (anions). Cation exchange resins will bind to positively charged molecules, displacing the counter-ion.

The phrase "viral inactivation", as used herein, refers to a decrease in the activity of adventitious enveloped viruses in a particular sample ("inactivation"). Such decreases in the activity of enveloped viruses can be on the order of about 3 log reduction factor (LRF) preferably of about 4 LRF, more preferably of about 5 LRF, even more preferably of about 6 LRF.

Any one or more of a variety of methods of viral inactivation can be used including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire teaching of which is incorporated herein by reference.

Methods of pH viral inactivation include, but are not limited to, incubating the mixture for a period of time at low pH, and subsequently neutralizing the pH. In certain embodiments the mixture will be incubated at a pH of between about 2 and 5, preferably at a pH of between about 3 and 4, and more preferably at a pH of about 3.6.

The pH of the sample mixture may be lowered by any suitable acid including, but not limited to, citric acid, acetic acid, caprylic acid, or other suitable acids. The choice of pH level largely depends on the stability profile of the antibody product and buffer components. It is known that the quality of the target antibody during low pH virus inactivation is affected by pH and the duration of the low pH incubation. In certain embodiments the duration of the low pH incubation will be from 0.5hr to 2hr, preferably 0.5hr to 1.5 hr, and more preferably the duration will be about 1hr. Virus inactivation is dependent on these same parameters in addition to protein concentration, which may limit inactivation at high concentrations.

Thus, the proper parameters of protein concentration, pH, and duration of inactivation can be selected to achieve the desired level of viral inactivation.

In certain embodiments viral filtration is performed. This can be achieved via the use of suitable filters. A non-limiting example of a suitable filter is the Ultipor DV50™ filter from Pall Corporation. In certain embodiments, alternative filters are employed for viral inactivation, such as, but not limited to, Sartorius filters, Viresolve™ filters (Millipore, Billerica, Mass.); Zeta Plus VR™ filters (CUNO; Meriden, Conn.); and Planova™ filters (Asahi Kasei Pharma, Planova Division, Buffalo Grove, Ill.).

Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size that allow transfer of protein with average size of 50 kDa (for example) or smaller. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained antibody. In certain embodiments of the present invention, a diafiltration step is employed to exchange the various buffers used in connection with the instant invention, optionally prior to further chromatography or other purification steps, as well as to remove impurities from the antibody.

In one embodiment, the antibody which is isolated is crystallized.

As used herein the term "crystallizing" refers to the solidification of the molecule of interest so as to form a regularly repeating internal arrangement of its atoms and often external plane faces.

Several crystalization approaches which are known in the art can be applied to the sample in order to facilitate crystalization of the molecule of interest. Examples of crystallization approaches include, but are not limited to, the free interface diffusion method [Salemme, F. R. (1972) Arch. Biochem. Biophys. 151:533-539], vapor diffusion in the hanging or sitting drop method (McPherson, A. (1982) Preparation and Analysis of Protein Crystals, John Wiley and Son, New York, pp 82-127), and liquid dialysis (Bailey, K. (1940) Nature 145:934-935).

Presently, the hanging drop method is the most commonly used method for growing macromolecular crystals from solution; this approach is especially suitable for generating protein crystals. Typically, a droplet containing a protein solution is spotted on a cover slip and suspended in a sealed chamber that contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

In another embodiment, the protein is subjected to 2D gel electrophoresis.

The agents used for purifying the antibody may be provided as a kit.

Thus, according to yet another aspect of the present invention there is provided a kit for purifying a protein comprising a hydrophobic chelator, a metal ion, a non-ionic detergent and a buffer having a pH between 3-6.

These components have been described herein above.

In an alternative arrangement, the kit may comprise a hydrophobic chelator, a polysorbate surfactant and metal ions.

The hydrophobic chelator is preferably packaged in a separate container to the metal ion.

The kit may also comprise a protease inhibitor.

Protease inhibitors include serine protease inhibitors, cystein protease inhibitorsaspartic protease inhibitors and metallo-protease inhibitors.

In one embodiment, the kit comprises at least two, at least three, at least four, at least five, at least six protease inhibitors.

Examples of protease inhibitors include, but are not limited to AEBSF, Bestatin, E-64, Pepstatin A, Phosphoramidon, Leupeptin and Aprotinin.

The protease inhibitors may be packaged separately or in a single container (i.e. as a cocktail).

Protease inhibitor cocktails are commercially available, for example from Sigma Aldrich.

Preferably, the containers of the kits of this aspect of the present invention include a label. Suitable containers include, for example, bottles, vials, syringes, and test tubes. The containers may be formed from a variety of materials such as glass or plastic.

In addition, other additives such as stabilizers, buffers, blockers and the like may also be added.

It is expected that during the life of a patent maturing from this application many relevant hydrophobic chelators will be developed and the scope of the term hydrophobic chelator is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8$^{th}$ Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Materials: Tween-20 (polysorbate 20), mouse IgG, bathophenathroline, NaCl, $FeSO_4$, $ZnCl_2$, $NiBr_2$ were obtained from Sigma-Aldrich (St. Louis, MO). Human IgG was from LeeBiosolutions—St. Louis, Missouri, USA.

Preparation of Tween-20 aggregates: Tween-20 aggregates were obtained by mixing equal volumes of medium A and B: Medium A was prepared by the addition of 10 µL of the hydrophobic chelator bathophenanthroline (20 mM in methanol) to 90 µL of 0.25 mM Tween-20 with vigorous vortexing to a final volume of 100 µL. An equal volume of medium B, comprised of 1mM $FeSO_4$ in 20mM NaCl was then added to Medium A with vigorous vortexing.

Purification of hIgG and mouse IgG with Tween-20 aggregates: A mixture containing *E. coli* lysate (5 µL) and the target IgG (5 µL) was added to preformed Tween-20 aggregates and incubated for 5 minutes at room temperature (or 4° C.). Centrifugation (13K, 2 minutes) was applied, the supernatant discarded and the pellet was briefly washed with 100 µL of cold 20 mM NaCl. Pellets were dissolved in the presence of sample buffer and analyzed by SDS-PAGE.

Extraction of IgG's from Tween-20 aggregates: Tween-20 pellets containing the target IgG were generated as described and further incubated with 50 µL of either: 50 mM NaOAc (pH 4.6)\20 mM NaCl or 50 mM Gly (pH 4)\20 mM NaCl. After 5-10 minutes at room temperature (or 4° C.), samples were neutralized, loaded on the gel or analyzed by CD.

Light microscopy: Images were obtained using an Olympus CX-40 light microscope equipped with an Olympus U-TV1X-2 digital camera.

Cryo-TEM analysis: Samples (10 µl) for cryo-TEM were prepared in the controlled environment vitrification system (CEVS), equilibrated at 25° C. and at saturation. Vitrified specimens were examined in an FEI T12 $G^2$ TEM operating at 120 kV. Images were recorded under low dose conditions as described previously. [27, 28] Measurements on the cryo-TEM images were made with ImageJ (imagej(dot)nih(dot)gov) software.

Circular dichroism (CD) spectroscopy: Antibodies that were extracted from Tween-20 aggregates as described above were subjected to CD analysis using a Chirascan CD spectrometer (Applied Photophysics). The CD spectra report ellipticity θ, which is proportional to the difference in absorbance of left and right circularly polarized light [θ=3300° (AL-AR)20] as a function of wavelength. A quartz 1×1 cm path length cuvette was used. The CD spectra were recorded with 1 nm bandwidth resolution in 1 nm steps at 20° C. The CD spectra were corrected for baseline distortion by subtracting a reference spectrum of the corresponding buffer.

Densitometry: Bands present in Coomassie stained gels were quantified using the EZQuant program.

Results

Conjugation of Tween-20 micelles: Addition of the hydrophobic chelator: bathophenanthroline to an aqueous solution containing Tween-20 micelles was followed by the addition of $Fe^{2+}$ ions serving as the mediator in the aqueous phase. Phase separation, in the form of red granular precipitates, were observed after a few minutes of incubation at room temperature (FIG. 2A). Control experiments in the absence of $Fe^{2+}$ resulted in elongated micro-crystals—presumably comprised of the hydrophobic chelator: bathophenanthroline (FIG. 2B. Additional controls in the absence of only the chelator or both the chelator and the metal, did not induce any phase separation (i.e. the drop was clear, not shown). Analysis of the resulting red aggregates with cryo-TEM showed that the detergent and the metal (dark spots in FIG. 2C) generated condensed aggregates with irregular shapes and sizes (FIG. 2C), whereas in a control experiment, devoid of the [(bathophenanthroline)3:$Fe^{2+}$] hydrophobic complex, micelles were uniformly distributed and no phase separation was observed (FIG. 2D).

Process specificity and dependence on low ionic strength: A brief incubation (5 minutes) of hIgG with conjugated Tween-20 micelles (i.e. Tween-20 aggregates), followed by a short centrifugation step (13K, 2 min.) led to a condensed red pellet, allowing efficient supernatant removal. SDS-PAGE analysis of the pellets indicated that they contain the reduced heavy and light chains (FIG. 3A, lane 3). Moreover, the majority (>85% by densitometry) of impurities that were present in the system are absent in the pellet (compare lanes 1 and 3 in FIG. 3A). Control experiments, in the absence of only the chelator or only the metal, resulted in significant reduction of the amounts of the reduced heavy and light chains (FIG. 3A, lanes 4-5, respectively). Tween-20 aggregates, without protein (i.e. impurities or IgG's) were stained as well by Coomassie (FIG. 3A, lane 6) and migrated to the band observed at the front of the gel in lane 3 (see asterisk).

Figure 3B:
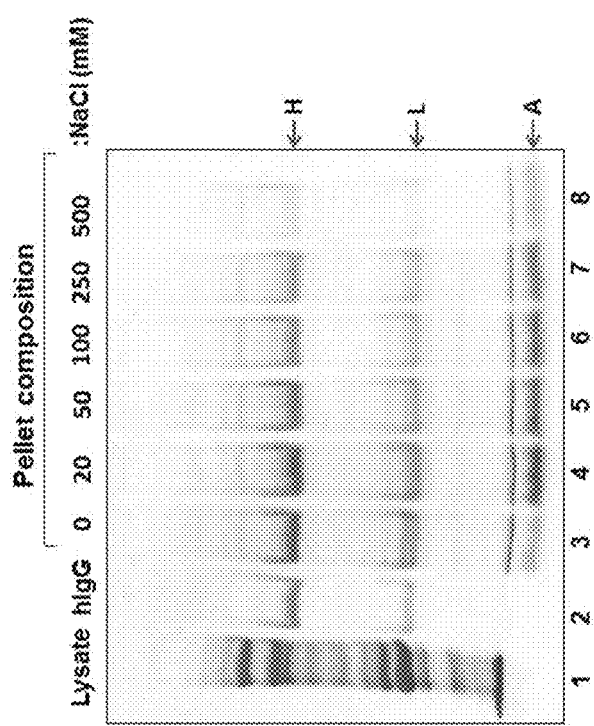
Figure 3C:
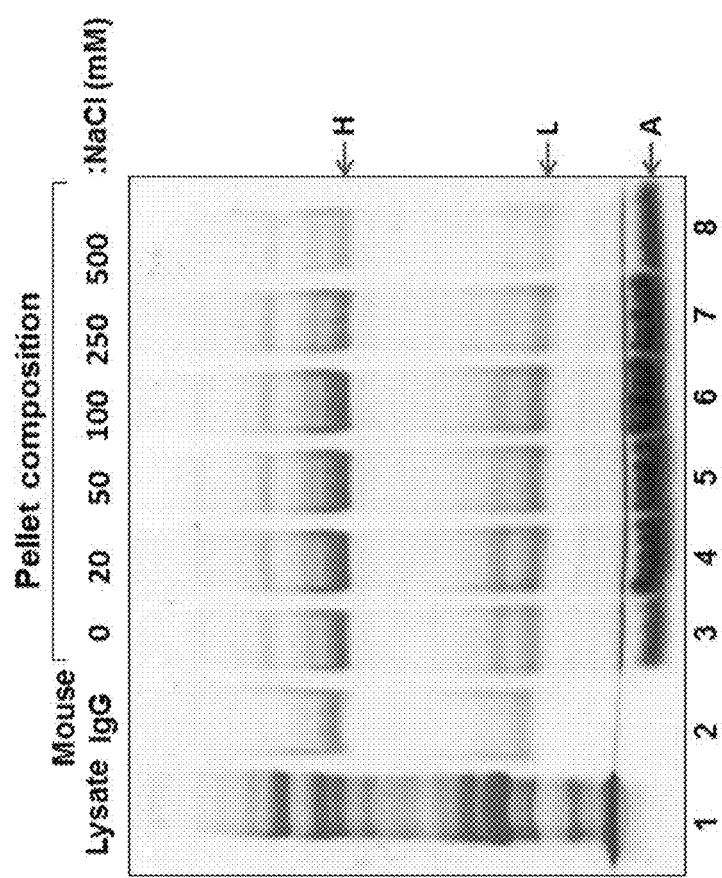

The effect of ionic strength is shown in FIG. 3B. It was found that, at relatively low salt concentrations (e.g. 20 mM NaCl), hIgG capture was efficient (FIG. 3B, lanes 3-4) whereas at higher salt concentrations (50-500 mM), process efficiency was progressively suppressed (FIG. 3B, lanes 5-8). The reduction in both the heavy and light chains with increasing ionic strength was found to apply as well to the bands representing the detergent aggregates (FIG. 3B, lanes 4-8). Similar results and general intensity trends were also observed when the target IgG was from mouse (FIG. 3C).

Figures 4A, 4B:
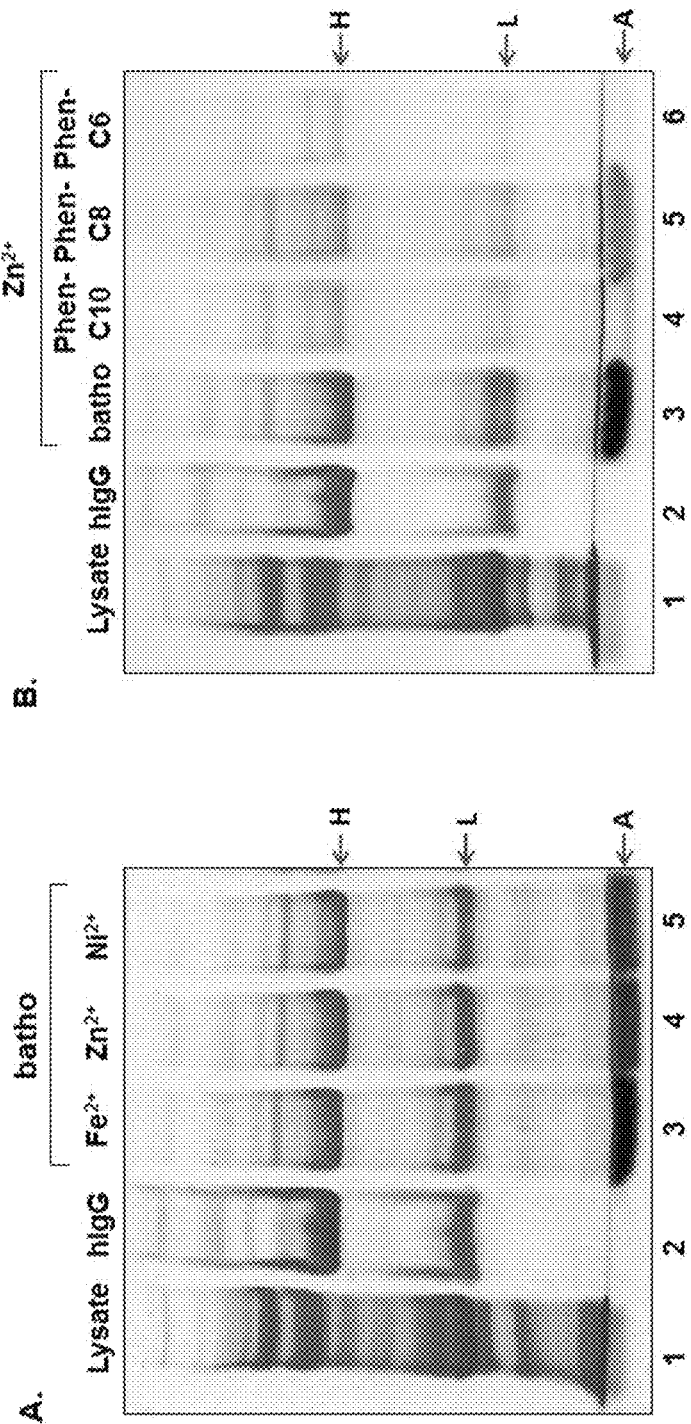
FIGS. 4A-C illustrate the process efficiency in the presence of different divalent metal cations: Lane 1: *E. coli* lysate; lane 2: Target hIgG; lane 3: pellet composition in the presence of the [(bathophenanthroline)$_3$:$Fe^{2+}$] complex; lanes 4-5: as in lane 3 but in the presence of $Zn^{2+}$ and $Ni^{2+}$, respectively. B. Process efficiency in the presence of synthesized 1,10-phenanthroline derivatives. Lane 1: *E. coli* lysate; lane 2: Target hIgG; lanes 3-6: pellet composition in the presence of: bathophenanthroline, Phen-C10, Phen-C8 and Phen-C6, respectively. C. Chemical structure of the chelators used. The gel is Coomassie stained.
Figure 4C:
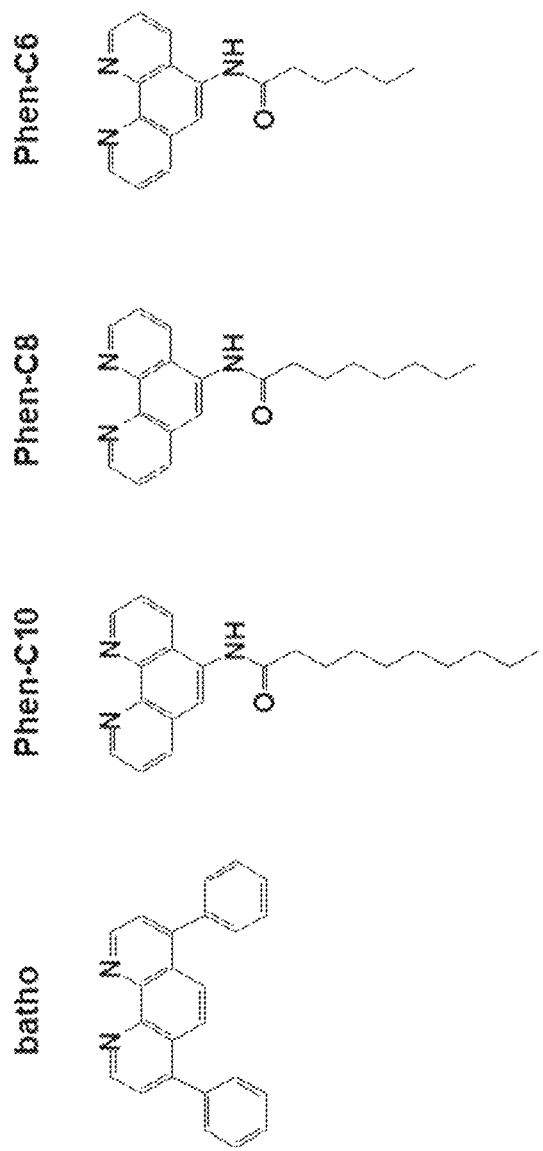

Applicability to other metals and hydrophobic chelators: Two additional ions (i.e. $Zn^{2+}$ and $Ni^{2+}$) known to bind three bathophenanthroline moieties in parallel, were studied as well. The results obtained with $Zn^{2+}$ were very similar to those found with $Fe^{2+}$ whereas $Ni^{2+}$ ions, led to lower yields in comparison to either $Fe^{2+}$ or $Zn^{2+}$ (FIG. 4A, lanes 3-5). Changes in the hydrophobic moiety of the chelator, were found to have a profound effect. The use of three synthesized 1,10-phenanthroline analogs, containing: 6, 8 or 10 carbon chains instead of the two phenyl groups, in the commercially available bathophenanthroline (FIG. 4C), show that the yield of the process is dramatically decreased (FIG. 4B, lanes 3-6).

Extraction of hIgG and mouse IgG from Tween-20 aggregates; CD analysis: Target hIgG (or mouse IgG) were extracted from Tween-20 aggregates using two different buffer systems: 50 mM NaOAc (pH 4.6) or 50 mM Gly (pH 4). The presence of NaCl was found to greatly affect the extraction efficiency. In the absence of NaCl, the supernatant contained the antibody and detergent aggregates with both tested buffers (FIG. 6A, lanes 3 and 6). However, the addition of 10-20 mM NaCl, greatly suppressed the water-solubility of the Tween-20 aggregates and in parallel, reduced the concentration of the antibody (FIG. 6A, lanes 4-5 and 7-8). Densitometry measurements indicate that, the overall yield of the process (i.e. partitioning & extraction) when NaOAc (pH 4.6) or Gly (pH 4) were used, ranged between: ~42-46% and ~40-46%, respectively, with minimum dissolution of aggregates (not shown).

The general trends with mouse IgG, were similar (FIG. 6B). Here again, the presence of NaCl suppressed the water-solubility of Tween-20 aggregates, however, the extraction yields were poorer than those obtained with hIgG and ranged between 28-15% for NaOAc buffer and 22-13% for Gly buffer (FIG. 6B).

The CD spectrum obtained from hIgG that was subjected to the Tween-20 aggregate process does not show any significant changes in the secondary structure of the purified antibody (FIG. 6C).

Discussion

This study explores the possibility of purifying IgG's with conjugated Tween-20 micelles as an alternative to the commonly used: ProA columns. The experimental findings demonstrate that, micelles comprised of the non-ionic detergent Tween-20 (Polysorbate 20) can be specifically conjugated in the presence of the hydrophobic [(bathophenanthroline)$_3$:$Fe^{2+}$] red complex, leading to granular red precipitates (FIG. 2A). Micellar conjugation was found to be highly specific as it did not occur in the absence of either the metal (FIG. 2B) or the chelator (not shown). In the absence of $Fe^{+2}$, crystals of the hydrophobic chelator are observed (FIG. 2B). Analysis of the red-colored aggregates with cryo-TEM show that the [(bathophenanthroline)$_3$:$Fe^{2+}$] complex leads to various aggregational forms, some of which reach 100 nm (FIG. 2C) in size, whereas in the absence of the complex, the micellar dispersion appears monodisperse (FIG. 2D). These results provide direct evidence for the ability of the [(bathophenanthroline)$_3$.$Fe^{2+}$] complex to induce micellar clustering.

To demonstrate IgG purification, a mixture of the target IgG in *E. coli* lysate (which served as an artificial contamination background) was added to preformed Tween-20 aggregates. After 5 min incubation, the mixture was centrifuged and impurities present in the supernatant, were discarded. Analysis of the pellet by SDS-PAGE revealed the presence of the reduced heavy and light chains (FIG. 3A, lane 3). This was the first indication of the capability of Tween-20 aggregates to capture hIgG from complex mixtures. Moreover, the vast majority of impurities present in the system (FIG. 3A, lane 1) were absent in the pellet (FIG. 3A, lane 3), consistent with the hypothesis that water-soluble proteins other than IgG (which are on average more polar than IgG), would not associate with Tween-20 aggregates whereas antibody molecules would associate.

The dependence of the process on the chelator and metal is shown in lanes 4 and 5 in FIG. 3A. In the absence of only the chelator, the intensity of the bands corresponding to the heavy and light chains is dramatically reduced (FIG. 3A, lane 4). Similar results were observed in the absence of only the metal (FIG. 3A, lane 5). Both findings suggest that when no metal or chelator is present, detergent aggregates, into which hIgG spontaneously partition, are not generated, explaining the dramatic reduction in process efficiency (FIG. 3A, lanes 4-5). An unexpected band appeared in lane 3, at the front of the gel (see asterisk in FIG. 3A, lane 3).

This band seemed to derive from the pellet but it does not appear in the *E. coli* lysate (FIG. 3A, lane 1) or in the target hIgG (FIG. 3A, lane 2). Hence, its identity was unclear, until Tween-20 aggregates, devoid of protein, were loaded on the gel (FIG. 3A, lane 6). These aggregates were found to be stained by Coomassie dye and to migrate as the band observed in lane 3. All these results demonstrate the mandatory requirement for the [(bathophenanthroline)3:$Fe^{2+}$] complex and the capability of Tween-20 aggregates to capture IgG while the majority of non-IgG proteins remain in the supernatant.

During process optimization, it became apparent that ionic strength has a dramatic effect on the yield. At low ionic strength (0-20 mM) the process was highly efficient (FIG. 3B, lane 4) whereas at higher salt concentrations the process gradually became inefficient (FIG. 3B, lanes 5-8).

This trend is clearly seen when the intensities of the bands corresponding to the heavy (or light) chains as a function of salt concentration, are compared (FIG. 3B, lanes 4-8). This phenomenon can be explained by analyzing the behavior of the detergent aggregates at different salt concentrations. Tween-20 aggregates are at their lowest water-solubility when 20 mM NaCl are added (FIG. 3B, lane 4) and at their highest water-solubility when 500 mM NaCl are present (FIG. 3B, 8). This behavior can explain why high and low hIgG recovery yields are obtained at low and high ionic strengths, respectively. Thus, a simple correlation between process efficacy (i.e. yield of hIgG capture) and the water-solubility of the Tween-20 aggregates was found.

To demonstrate the potential generality of the process, the present inventors studied the dependence of IgG partitioning behavior with polyclonal mouse IgG as well (FIG. 3C) and found a very similar pattern. The fact that IgG from different biological origins (human and mouse) partition efficiently into Tween-20 aggregates implies that our purification strategy may be independent of the particular amino acid sequence of the target IgG. This, in turn, may circumvent the need to develop specific purification protocols for each therapeutic monoclonal antibody and thus, a standardized purification platform may be achieved. Replacement of $Fe^{2+}$ ions with $Zn^{2+}$ led to similar results with respect to purity and yield (FIG. 4A, lane 4), whereas the use of $Ni^{2+}$ ions appeared to be less efficient (FIG. 4A, lane 5). The fact that $Zn^{2+}$ ions generate similar results to those obtained by $Fe^{2+}$ is encouraging as it broadens the scope of possible components. However, exchanging the commercial chelator: bathophenanthroline, with either of the three synthesized 1,10-phenanthroline analogs, containing 6, 8 and 10 carbon tails: Phen-C10, Phen-C8 and Phen-C6 (FIG. 4C) emphasized the advantage of the two phenyl groups in bathophenanthroline over long alkyl tails.

Since densitometry measurements indicated that, the partitioning yield of hIgG or mouse IgG into Tween-20 aggregates (under ideal salt conditions), is essentially quantitative (~95%), it can be argued that, such aggregates may provide a viable alternative to ProA columns commonly used in the large-scale downstream processing of therapeutic grade mAb's (FIG. 5A). If indeed the ProA column could be removed from the equation and replaced by Tween-20 aggregates (FIG. 5B), then after IgG partitioning into the aggregates, the supernatant containing the majority of impurities could be removed, the pellet dissolved and the target mAb would then be subjected to the two commonly used ion exchangers, as the final polishing steps (FIG. 5B).

Clearly, removal of one of the three traditional chromatographic steps (i.e. the ProA column), is expected to facilitate mAb production and hence, increase the cost-effectiveness of the entire purification process. Following this rationale, the present inventors considered whether it would be possible to remove two chromatographic steps of the three, i.e.

one of the ion exchanges as well, since that would further increase production efficiency. Such an objective could only be considered if one could generate IgG preparations with significantly greater purity than those presented in FIGS. 3A-C and 4A-C. The present inventors therefore assessed the possibility of extracting IgG embedded in Tween-20 aggregates into a fresh buffer solution, while suppressing the dissolution of the detergent aggregates and\or the extraction in parallel of hydrophobic entities that may be present in the aggregates as well.

Two buffer systems (NaOAc pH 4.6 and Gly pH 4) demonstrated their capability in extracting hIgG and mouse IgG from Tween-20 aggregates while significantly suppressing aggregate dissolution and concomitant extraction of hydrophobic impurities (FIGS. 6A-B). A dramatic effect of the NaCl concentration on the water-solubility of Tween-20 aggregates was observed once again. When pellets containing hIgG were incubated with 50 mM NaOAc (pH 4.6) in the absence of added NaCl, the supernatant contained a relatively pure IgG but also a significant amount of dissolved Tween-20 aggregates (FIG. 6A, lane 3). The addition of 10 mM NaCl significantly suppressed the detergent aggregate solubility but in parallel reduced the concentration of hIgG in the supernatant (FIG. 6A, lane 4). Further addition of salt, seemed to completely abolish detergent dissolution but resulted in poor recovery yields of hIgG (FIG. 6A, lane 5). When the buffer system was comprised of Gly (pH 4) improved recovery yields were observed (FIG. 6A, lane 8).

Densitometry measurements indicate that the overall yield for the two steps (i.e. partitioning & extraction) with either NaOAc or Gly buffers range between 40-46%. These values represent conditions in which there is no evidence for the presence of the micellar aggregate in the supernatant. The purity of extracted hIgGs in lane 8 (for example) is comparable to that of lane 2. Since the latter represents purity >99% (by the manufacturer) it implies that, without chromatography and without the use of ProA, significantly greater purity could be achieved if the extraction efficiency could be further improved. This might pave the way for the removal of two chromatographic steps out of the three currently employed. Lower extraction efficiency was observed with mouse IgG (FIG. 6B). However, the general impact of salt concentration on the water solubility of Tween-20 aggregates containing mouse IgG was similar to that obtained with hIgG.

Preservation of the secondary structure of hIgG was studied with circular dichroism (CD) (FIG. 6C). The CD analysis indicates that, no significant changes occurred in the secondary structure of purified hIgG (FIG. 6C).

Conclusions

Two potential non-chromatographic processes capable of purifying IgG's without the use of ProA as a ligand were presented. Whereas high yields and lower purity are obtained by the spontaneous partitioning of antibodies into Tween-20 aggregates followed by aggregate dissolution, lower recovery yields and higher purity are achieved after a short extraction step. The strategy seems to be independent of the specific sequence of the target antibody and as such may provide a standardized purification platform. The granular texture of Tween-20 aggregates is expected to allow filtration (for example) and thus implementation of the process in a continuous purification process.

Example 2

Purification of Human & Mouse IgG's in Serum Free Media

Figures 7A, 7B:
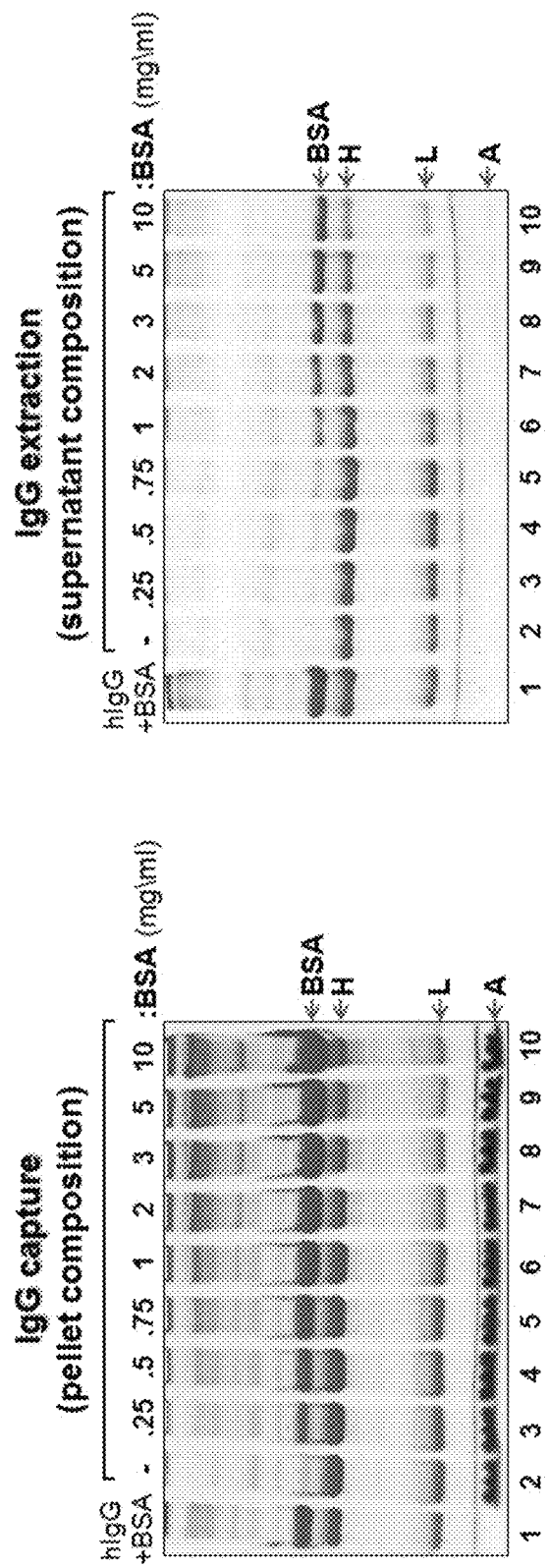
FIGS. 7A-D illustrate the effect of BSA on purification of human & mouse IgG's in serum-free media. A. Human IgG (hIgG) capture: Lane 1: hIgG and BSA; lanes 2-10: Pellet composition obtained after incubating Tween-20 aggregates with hIgG (1 mg\ml) and indicated BSA concentrations in serum free-media as described in the Experimental. B: Supernatant composition after incubating the corresponding pellets generated in Gel A-I (lanes 2-10) with 50mM isoleucine at pH 3.8 as described in the Experimental. C and D as described in A but in the presence of mouse IgG. The letters: H & L represent the reduced Heavy and Light chains of the target antibody, respectively. The letter A, points at the detergent aggregate band. Gels are coomassie stained.
Figures 7C, 7D:
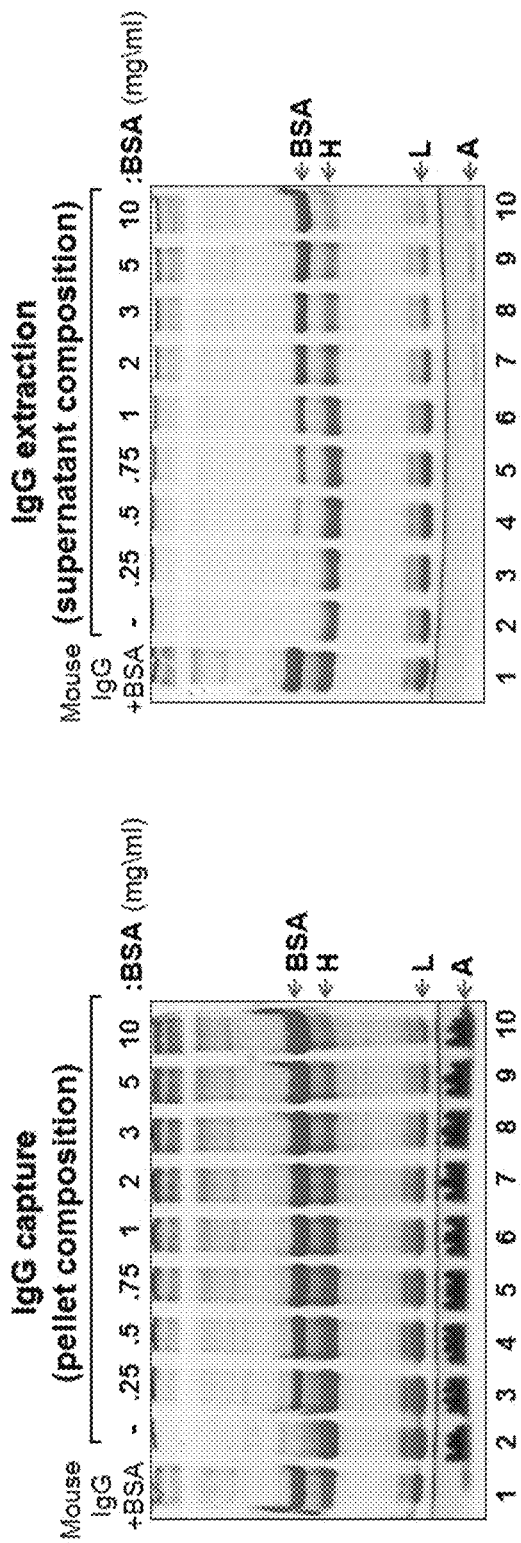

Completion of optimizations trials in the presence of *E. coli* lysate, paved the way towards implementation of the method in hybridoma serum-free media. Both, hIgG and mouse IgG's were observed in Tween-20 pellets. (FIG. 7A and 7C) Inclusion of BSA or HSA at concentrations higher than 0.5 mg/ml (in addition to the target IgG), was found to suppress progressively IgG binding concomitant to an increase of the albumin concentration within the aggregates. (FIG. 7A and 7C).

Of particular importance, was the finding that, human and moues IgG's could be extracted from Tween-20 aggregates with 50mM isoleucine (pH 3.8) without significant co-extraction of BSA nor aggregate dissolution. (FIGS. 7B and 7D: lanes 3-4) At higher BSA concentration (≥0.5 mg\ml), the albumin was observed in the extracted IgG. (FIGS. 7B and 7D: lanes 5-10). Similar results were observed when BSA was replaced by HSA (not shown).

Under optimal conditions, the yields of IgG capture ranged between: 80-90% for hIgG\BSA, 76-79% for mouse IgG\BSA, 67-55% for hIgG\BSA and 75-78% for mouse IgG\HSA, as summarized in Table 1, herein below.

TABLE 1

| | process efficiency | |
|---|---|---|
| | IgG capturing yield* | Overall yield (IgG capture + extraction)* |
| Human IgG\BSA | 77-85% | 59-64% |
| Human IgG\HSA | 80-88% | 58-64% |
| Mouse IgG\BSA | 80-87% | 52-61% |
| Mouse IgG\HSA | 77-82% | 50-54% |

*The range of values rely on 3-5 independent experiments

The overall yield of the two step process (i.e. IgG partitioning+extraction) ranged between 54-63% and was shown to be more efficient when BSA rather than HSA.

Example 3

Extraction Buffers, Circular Dichroism (CD) and Dynamic Light Scattering (DLS)

Extraction buffers, comprised of different amino acids (all at pH 3.8), were studied. Highest recovery yields were obtained with: Gly, Val or Ile buffers (FIG. 8A: lanes 3-5) while Arg or His buffers were found to be less efficient (FIG. 8A: lanes 6-7). The use of Asp or Glu buffers, promoted partial aggregate dissolution. (FIG. 8A: lanes 8-9, see bands at the front of the gel).

Incubation at 32° C. led to the highest extraction yields when compared to lower temperatures (4-19° C., not shown) and did not seem to represent a concern since therapeutic mAb's were reported to undergo chemical modification at higher temperatures (e.g. 37° C., pH 4.5) and longer incubation times (1-4 days).

Dynamic light scattering (DLS) measurements did not show any change in size between purified and control IgG's nor the existence of particles greater than the IgG itself. (FIGS. 8B and 8C) The fact, that, these results repeated themselves with three extraction buffers and two IgG populations (human and mouse), suggests that IgG extraction can be achieved without concomitant aggregate dissolution.

Figure 8D:
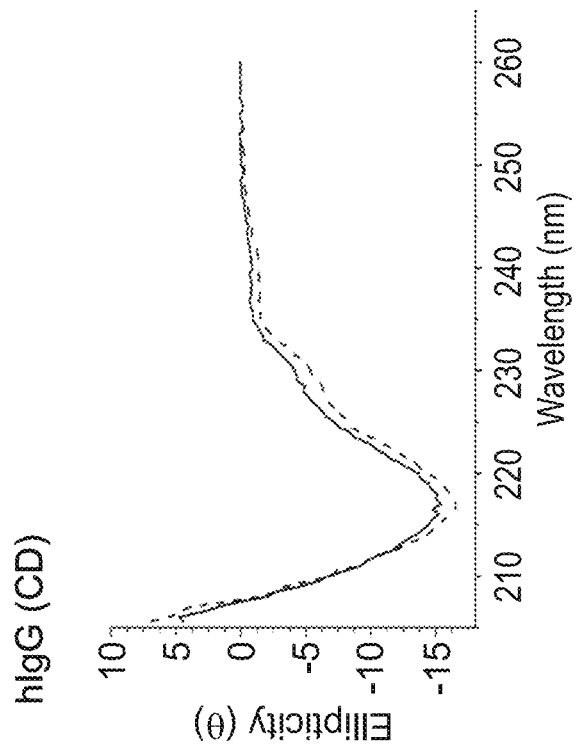

Comparison of the CD spectrum of hIgG's that were subjected to purification with Tween-20 aggregates and extracted with Gly buffer to those that were not (i.e. control hIgG) showed, that, both spectrums are very similar, represent the prominent secondary structure of IgG's (i.e. anti-parallel beta-sheets [18]) with the negative absorption at:

−218 nm [19] and are in agreement with previous reports [20] (FIG. 8D). Since, similar spectra were also obtained with mouse IgG (FIG. 8E) implies, that, the presented purification approach is mild and preserved the secondary structure of tested IgG's.

Example 4

Preservation of IgG Specificity (ELISA Assays)

Preservation of IgG specificity at the end of the purification process was studied with two types of polyclonal antibodies (Sheep & Rabbit) that recognize: BSA. Each of these Ab's was purified with Tween-20 aggregates (containing HSA and not BSA, to eliminate BSA from the system), extracted with each of the 7 studied buffers (one at a time) and finally, tested for their ability to bind their target: BSA in an ELISA assay. Differences in the observed ELISA signals (FIGS. 9A-B), reflect differences in extraction efficiency as had been observed with hIgG and mouse IgG. Highest signals were obtained when extraction buffers were composed of Asp or Glu. These findings are consistent with those described earlier, where it was shown that Asp and Glu buffers induce partial aggregate dissolution (FIG. 8A: lanes 8-9), lead to higher IgG concentration that immediately explains the stronger ELISA signals (FIGS. 9A-B).

Example 5

Purification of IgM with Tween-20 Aggregates

Materials and Methods

IgM capture by Tween-20 aggregates: Tween-20 aggregates were generated by incubating: 0.1125 mM Tween-20, 1 mM bathophenanthroline, 0.5 mM $FeSO_4$ and 10 mM NaCl for 10 minutes at room temperature. A mixture of IgM and BSA (IgM\BSA) was then added to the freshly prepared Tween-20 aggregates and the system was further incubated for 10 minutes at room temperature. The IgM\BSA mixture, was prepared by dissolving polyclonal IgM (Sigma—I8135) with BSA (Sigma—A2153) in Ex-CELL medium (Sigma—H4281) where both the IgM and BSA were at 0.5 mg\ml. Centrifugation (13,000 rpm, 5 min), allowed removal of the supernatant, the resulting pellets were washed with 50 µl of cold 20 mM NaCl and the pellet composition was analyzed by SDS-PAGE.

IgM Extraction From Tween-20 Aggregates

Pellets containing captured IgM were subjected to acidic conditions (50 mM Isoleucine pH 3) and incubated for 30 minutes at 32° C. Samples were centrifuged (13,000 rpm, 5 min) and the composition of supernatant (i.e. the extract) was analyzed by SDS-PAGE.

Results

This conclusion is supported by the finding that a brief incubation (5 minutes) of Tween-20 aggregates with a mixture of: [IgM+BSA] followed by removal of the supernatant leads to pellets that contain the reduced heavy & light chains of the target IgM (FIG. 10A lane 5). Process efficiency is totally dependent on the presence of both the chelator (batho) and the metal (Fe2+) since in their absence, no IgM is detected in the Tween-20 pellets (FIG. 10A lanes 6-7, respectively).

These results can be explained by the need for a hydrophobic or semi-hydrophobic environment onto which IgM antibodies adsorb\bind. Thus, the absence of the chelator (batho) or the absence of the metal (Fe2+), maintain Tween-20 micelles independent i.e., unconjugated and hence, no hydrophobic environment for IgM binding\partitioning exists (FIG. 10A, lanes 6-7).

IgM antibodies can be extracted from pellets containing IgM without concomitant dissolution of the pellets (i.e. the Tween-20 aggregates). This is achieved by incubating pellets at 32° C. for 30 minutes under acidic conditions (50 mM Isoleucine, pH 3) and is followed by centrifugation that removes immiscible particles from the supernatant. SDS-PAGE analysis of the supernatant indicates that the reduced heavy and light chains of the IgM are present in the supernatant without detectable amounts of Tween-20 aggregates (FIG. 10B lanes 4-7).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Aggarwal, R. S., *What's fueling the biotech engine*-2012 to 2013. Nat Biotechnol, 2014. 32(1): p. 32-9.
2. Wurm, F. M., *Production of recombinant protein therapeutics in cultivated mammalian cells.* Nat Biotechnol, 2004. 22(11): p. 1393-8.
3. Low, D., R. O'Leary, and N. S. Pujar, *Future of antibody purification.* J Chromatogr B Analyt Technol Biomed Life Sci, 2007. 848(1): p. 48-63.
4. Gagnon, P., *Technology trends in antibody purification.* Journal of Chromatography A, 2012. 1221: p. 57-70.
5. <*Process scale antibody purification.pdf*>.
6. Shukla, A. A. and J. Thömmes, *Recent advances in large-scale production of monoclonal antibodies and related proteins.* Trends in Biotechnology, 2010. 28(5): p. 253-261.
7. Azevedo, A. M., et al., *Chromatography free recovery of biopharmaceuticals through aqueous two-phase processing.* Trends Biotechnol, 2009. 27(4): p. 240-7.
8. Roque, A. C., C. R. Lowe, and M. A. Taipa, *Antibodies and genetically engineered related molecules: production and purification.* Biotechnol Prog, 2004. 20(3): p. 639-54.
9. Wang, L., K. Z. Mah, and R. Ghosh, *Purification of human IgG using membrane based hybrid bioseparation technique and its variants: A comparative study.* Separation and Purification Technology, 2009. 66(2): p. 242-247.
10. Venkiteshwaran, A., et al., *Selective precipitation-assisted recovery of immunoglobulins from bovine serum using controlled-fouling crossflow membrane microfiltration.* Biotechnol Bioeng, 2008. 101(5): p. 957-66.
11. Kuczewski, M., et al., *A single-use purification process for the production of a monoclonal antibody produced in a PER.C6 human cell line.* Biotechnol J, 2011. 6(1): p. 56-65.

12. McDonald, P., et al., *Selective antibody precipitation using polyelectrolytes: a novel approach to the purification of monoclonal antibodies.* Biotechnol Bioeng, 2009. 102(4): p. 1141-51.
13. Kumar, A., et al., *Smart polymers: Physical forms and bioengineering applications.* Progress in Polymer Science, 2007. 32(10): p. 1205-1237.
14. Shukla, A. A., et al., *Downstream processing of monoclonal antibodies—application of platform approaches.* J Chromatogr B Analyt Technol Biomed Life Sci, 2007. 848(1): p. 28-39.
15. van Reis, R. and A. Zydney, *Bioprocess membrane technology.* Journal of Membrane Science, 2007. 297(1-2): p. 16-50.
16. Kelley, B., *Very large scale monoclonal antibody purification: the case for conventional unit operations.* Biotechnol Prog, 2007. 23(5): p. 995-1008.
17. Kelley, B., *Industrialization of mAb production technology: the bioprocessing industry at a crossroads.* MAbs, 2009. 1(5): p. 443-52.
18. Guse, A. H., et al., *Purification and analytical characterization of an anti-CD4 monoclonal antibody for human therapy.* J Chromatogr A, 1994. 661(1-2): p. 13-23.
19. Manzke, O., et al., *Single-step purification of bispecific monoclonal antibodies for immunotherapeutic use by hydrophobic interaction chromatography.* Journal of Immunological Methods, 1997. 208(1): p. 65-73.
20. Follman, D. K. and R. L. Fahrner, *Factorial screening of antibody purification processes using three chromatography steps without protein A.* J Chromatogr A, 2004. 1024(1-2): p. 79-85.
21. Ghosh, R. and L. Wang, *Purification of humanized monoclonal antibody by hydrophobic interaction membrane chromatography.* J Chromatogr A, 2006. 1107(1-2): p. 104-9.
22. Patchornik, G., et al., *Tethered non-ionic micelles: a matrix for enhanced solubilization of lipophilic compounds.* Soft Matter, 2012. 8(32): p. 8456-8463.
23. Patchornik, G., et al., *Purification of a membrane protein with conjugated engineered micelles.* Bioconjug Chem, 2013. 24(7): p. 1270-5.
24. Patchornik, G., et al., *Cryo-TEM structural analysis of conjugated nonionic engineered-micelles.* Soft Matter, 2014. 10(27): p. 4922-8.
25. Dutta, S., et al., *Engineered-membranes and engineered-micelles as efficient tools for purification of halorhodopsin and bacteriorhodopsin.* Analyst, 2015. 140(1): p. 204-12.
26. Martell, A. E. and R. M. Smith, *Critical stability constants.* 1974, New York: Plenum Press.
27. Danino, D., A. Bernheim-Groswasser, and Y. Talmon, *Digital cryogenic transmission electron microscopy: an advanced tool for direct imaging of complex fluids.* Colloids and Surfaces A: Physicochemical and Engineering Aspects, 2001. 183-185: p. 113-122.
28. Danino, D., *Cryo-TEM of soft molecular assemblies.* Current Opinion in Colloid & Interface Science, 2012. 17(6): p. 316-329.
29. Li, F., et al., *Cell culture processes for monoclonal antibody production.* MAbs, 2010. 2(5): p. 466-79.
30. Orellana, C. A., et al., *High-antibody-producing Chinese hamster ovary cells up-regulate intracellular protein transport and glutathione synthesis.* J Proteome Res, 2015. 14(2): p. 609-18.

What is claimed is:

1. A method of isolating an antibody, the method comprising:
   (a) contacting:
      (i) a chelator selected from the group consisting of bathophenathroline, Phen-C8 or Phen C-10,
      (ii) a non-ionic detergent: and
      (iii) metal ions selected from the group consisting of $Zn^{2+}$ and $Fe^{2+}$
   so as to generate an aggregate comprising said chelator, said detergent and said metal ions; and
   (b) contacting said aggregate with a medium comprising the antibody under conditions that allow partitioning of the antibody into said aggregate, thereby isolating the antibody.
2. The method of claim 1, wherein said medium comprises a cell lysate.
3. The method of claim 2, wherein said cell lysate is devoid of organelles greater than about 2 microns.
4. The method of claim 1, wherein said conditions of step (b) comprise having a level of salt below 100 mM.
5. The method of claim 1, further comprising solubilizing said antibody following step (b).
6. The method of claim 5, wherein said solubilizing is effected with a buffer having a pH between 3-6.
7. The method of claim 5, wherein said solubilizing is effected with a buffer having a pH between 3.8 and 4.
8. The method of claim 6, wherein said buffer further comprises a salt.
9. The method of claim 6, wherein said buffer is a carboxylic buffer.
10. The method of claim 6, wherein said buffer comprises an amino acid.
11. The method of claim 9, wherein said carboxylic buffer is selected from the group consisting of isoleucine, valine, glycine and sodium acetate.
12. The method of claim 1, wherein said non-ionic detergent is a polysorbate surfactant.
13. The method of claim 12, wherein said polysorbate surfactant is selected from the group consisting of polysorbate 20, polysorbate 40, polysorbate 60 and polysorbate 80.
14. The method of claim 1, wherein said chelator is a hydrophobic phenanthroline chelator is present in an aqueous solution at a concentration in the range of about 0.1% to about 10% (v/v).
15. The method of claim 1, wherein said metal ions are present in said aqueous solution at a concentration in the range of about 0.1% about 10% (v/v).
16. The method of claim 1, wherein said antibody is selected from the group consisting of IgA, IgD, IgE, IgM and IgG.

* * * * *